United States Patent
Pang et al.

(10) Patent No.: US 9,636,021 B2
(45) Date of Patent: May 2, 2017

(54) FLAVONOID COMPOUNDS OF LOW TOXICITY FOR BIOLOGICAL IMAGING APPLICATIONS

(71) Applicants: Yi Pang, Copley, OH (US); Bin Liu, Akron, OH (US)

(72) Inventors: Yi Pang, Copley, OH (US); Bin Liu, Akron, OH (US)

(73) Assignee: The University of Akron, Akron, OH (US)

(*) Notice: Subject to any disclaimer, the term of this patent is extended or adjusted under 35 U.S.C. 154(b) by 0 days.

(21) Appl. No.: 14/740,914

(22) Filed: Jun. 16, 2015

(65) Prior Publication Data

US 2015/0369812 A1    Dec. 24, 2015

Related U.S. Application Data

(60) Provisional application No. 62/012,582, filed on Jun. 16, 2014.

(51) Int. Cl.
| | | |
|---|---|---|
| *A61B 5/00* | (2006.01) | |
| *A61B 5/02* | (2006.01) | |
| *C07D 311/30* | (2006.01) | |
| *G01N 33/50* | (2006.01) | |
| *G01N 33/58* | (2006.01) | |

(52) U.S. Cl.
CPC ........ *A61B 5/0071* (2013.01); *A61B 5/02007* (2013.01); *C07D 311/30* (2013.01); *G01N 33/5088* (2013.01); *G01N 33/582* (2013.01); *A61B 2503/02* (2013.01); *A61B 2503/40* (2013.01); *G01N 2333/4603* (2013.01)

(58) Field of Classification Search
None
See application file for complete search history.

(56) References Cited

PUBLICATIONS

Gharpure et al. Synthesis of new series of 3-hydroxy/acetoxy-2-phenyl-4H-chromen-4-ones and their biological importance. 2013 J. Chem. Sci. 125: 575-582. Published May 2013.*
Jayashree et al. Synthesis of substituted 3-hydroxy flavones for antioxidant and antimicrobial activity. 2008 Pharmacologyonline 3: 586-595.*

* cited by examiner

*Primary Examiner* — Michael G Hartley
*Assistant Examiner* — Jennifer Lamberski
(74) *Attorney, Agent, or Firm* — Renner Kenner Greive Bobak Taylor & Weber

(57) ABSTRACT

Flavonoid compounds that are selective for a protein, a portion or a living cell, or a portion of an organism may be used as biological imaging agents. The flavonoid compounds are useful for methods of imaging organisms such as zebrafish embryos and zebra fish. Flavonoid compounds may also be used to detect protein. Advantageously, flavonoids that selectively bind protein, a portion of a living cell, or a portion of an organism may exhibit a florescence "turn-on" mechanism, where the flavonoids that are selectively bound exhibit a florescence response when excited.

15 Claims, 19 Drawing Sheets
(14 of 19 Drawing Sheet(s) Filed in Color)

Synthesis routes of flavone dyes 1-6

FLAVONOID COMPOUNDS OF LOW TOXICITY FOR BIOLOGICAL IMAGING APPLICATIONS

CROSS-REFERENCE TO RELATED APPLICATIONS

The present application claims priority to U.S. Provisional Patent Application No. 62/012,582, filed Jun. 16, 2014, incorporated herein by reference.

GOVERNMENT RIGHTS

This invention was made with government support under National Institutes of Health Grant No. 1R15EB014546-01A1. The government has certain rights in the invention.

FIELD OF THE INVENTION

The present invention relates to a biological imaging agent. The present invention further relates to flavonoids that selectively bind protein, a portion or a living cell, or a portion of an organism. The present invention further relates to an improved imaging reagent for imaging, developing cells, vascular systems, and detecting proteins.

BACKGROUND OF THE INVENTION

Over the last decades, in vivo fluorescent imaging has emerged as a powerful tool in biological studies, owing to its potential to visualize the dynamic processes of an organism development. In order to enable the technology, one has to find a practical biological imaging agent, or bioimaging agent, that can constantly recognize and track the specific biological target. In a typical process, fluorescent materials are linked to an antibody, protein, or mRNA to achieve good targetability, which often involves tedious procedures and high costs.

In recent years, the zebrafish (*Danio rerio*) has become a favorite model organism for studying vertebrate development, due to its prolific reproduction, transparency, and high homology with mammals. In the embryonic development of all teleost fishes, a remarkable feature is the formation of the yolk syncytial layer (YSL), an extra-embryonic tissue occurring at the surface of the yolk cell. YSL plays crucial roles in embryo patterning and morphogenesis, such as specifying mesoderm and endoderm cell fates in marginal blastomeres along the circumference of the embryo. It is also involved in the regulation of heart progenitor cell migration and essential metabolic functions.

In prior art YSL-imaging methods, non-diffusible fluorescent dyes (attached to either dextran or proteins) are injected into the top of the yolk close to yolk/blastoderm margin, where YSL is expected to develop. The injection process is normally carried out immediately before the YSL is formed. Since the YSL itself is a highly dynamic tissue undergoing extensive movements of overlying germ layer progenitor cells, it is very difficult to achieve accurate injection that can label the entire YSL region. The stability, targetability, and reliability of a fluorescent signal by using the above method are highly dependent on the original injection region, injection time, and injection dosage.

Based in part on the failures described above, imaging vascular systems remains a continuing challenge. Current methods for diagnostic imaging of the vascular system are dependent on magnetic resonance or digital subtraction angiography. The main limitation of conventional angiography is its invasiveness, since the procedure often requires percutaneous vessel cannulation with the introduction of intravascular wires and devices.

Attempts have been made to perform molecular imaging to visualize the fundamental biological processes in developing the vascular system. The imaging of the vascular system requires the imaging reagents to selectively absorp on the surface of blood vessels, whose fluorescence would provide a sharp image of the vessel. The reagents also need to be non-toxic. One current imaging reagent for vascular systems utilizes quantum dots, but leakage of toxic cadmium ion poses a health concern. In addition, the quantum-dots-based imaging reagents require injection, and only allow a short time period for imaging (about 0.5 hour after injection of imaging dye).

Currently methods of protein detection also suffer from several drawbacks. The detection and discrimination of different proteins with high sensitivity and selectivity are very important for biological studies and clinical diagnosis. Sodium dodecyl sulfate-polyacrylamide gel electrophoresis (SDS-PAGE) followed by western blotting is a current technique for protein analysis. The western blotting method has been widely used to separate, detect, and identify specific proteins in a complex mixture. However, in order to achieve the selective detection of a specific protein, time-consuming, multistep processes must be used. These processes also involve the use of expensive reagents and can require the protein transfer, blocking, and reaction with the primary and secondary antibodies, all followed by fluorescent detection of the bound antibodies. An essential step in western blotting is to stain the proteins following the separation by SDS-PAGE, where the post-stain washing is often necessary to remove the excess dyes. Therefore, it is highly desirable to develop new strategies that can facilitate protein visualization on a gel without going through a multiple steps process.

Among the known protein sensors, only few are capable of detecting proteins in gels. In addition, these dyes either exhibit low selectivity in responding to different proteins, or suffer from strong interference from SDS. The requirement and demand for improved staining can be seen from SYPRO Ruby, which is widely used for staining the proteins in SDS-PAGE. The standard process using SYPRO Ruby requires washing out the SDS, a long time for staining, and removing the excess dye. It is thus highly desirable to develop a simplified procedure that allows direct staining without the need for protein fixing, i.e. prior to staining, and washing out the non-bound staining reagent. Also, current staining methods generally display all proteins without discrimination.

Serum albumin is the most abundant protein in blood plasma and plays a key role in the disposition and transport of various endogenous ligands, fatty acids, and drugs. Some biological functions of serum albumin are associated with its natural hydrophobic pocket, which can be used to bind flavone dyes.

Thus, a need remains in the art for an improved biological imaging agent. A need also remains for a reliable and easy-to-use strategy for YSL imaging. A further need remains for an improved imaging reagent for displaying vascular systems.

SUMMARY OF THE INVENTION

In a first embodiment, the present invention provides a flavonoid compound defined by the formula

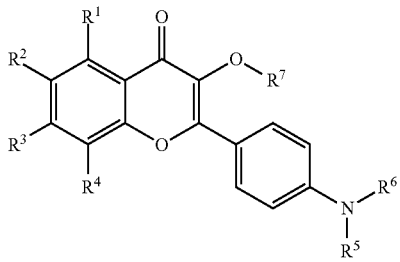

where each R1-R4 is individually an organic group or an hydrogen atom, each R5 and R6 is individually an organic group or an hydrogen atom or where R5 and R6 combine to form a single organic group, and R7 is an organic group.

In a second embodiment, the present invention provides a flavonoid compound as in the first embodiment, where the flavonoid compound is defined by the formula

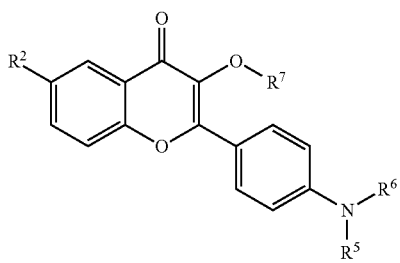

where R2 is an organic group or an hydrogen atom, each R5 and R6 is individually an organic group or an hydrogen atom or where R5 and R6 combine to form a single organic group, and R7 is an organic group.

In a third embodiment, the present invention provides a flavonoid compound as in either the first or second embodiment, where the flavonoid compound is defined by the formula

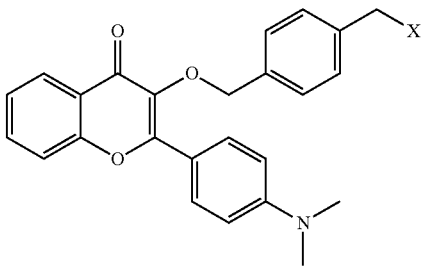

where X is a halogen atom.

In a fourth embodiment, the present invention provides a flavonoid compound as in any of the first through third embodiments, where the flavonoid compound is defined by the formula

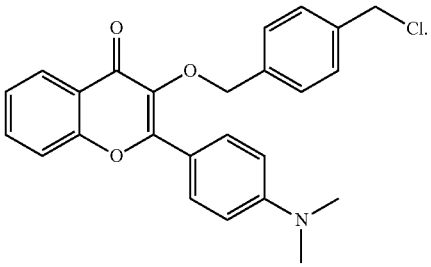 [SMILES: CN(C)c1ccc(-c2oc3ccccc3c(=O)c2OCc2ccc(CCl)cc2)cc1]

In a fifth embodiment, the present invention provides a method of imaging an organism comprising combining an organism with at least one cell and a flavonoid compound and allowing the flavonoid compound to permeate into the organism, where the flavonoid compound is defined by the formula

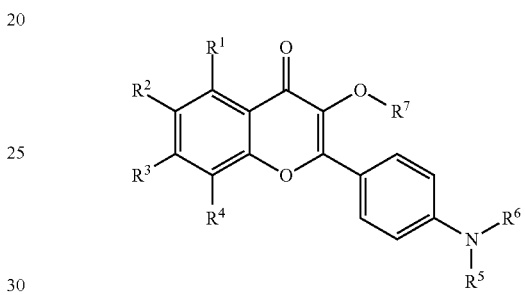

where each R1-R4 is individually an organic group or an hydrogen atom, each R5 and R6 is individually an organic group or an hydrogen atom or where R5 and R6 combine to form a single organic group, and R7 is an organic group; irradiating the organism with an excitation wavelength that excites the flavonoid and induces a fluorescence response; and capturing an image of the organism.

In a sixth embodiment, the present invention provides a method as in the fifth embodiment, where the organism is an embryo.

In a seventh embodiment, the present invention provides a method as in either of the fifth or sixth embodiments, where the embryo is a zebrafish embryo.

In an eighth embodiment, the present invention provides a method as in any of the fifth through seventh embodiments, where the step of combining the organism with a flavonoid is performed by preparing a media that includes the flavonoid and an organism.

In a ninth embodiment, the present invention provides a method of imaging a zebrafish, comprising providing an embryo media; adding a flavonoid compound to the embryo media, where the flavonoid compound is defined by the formula

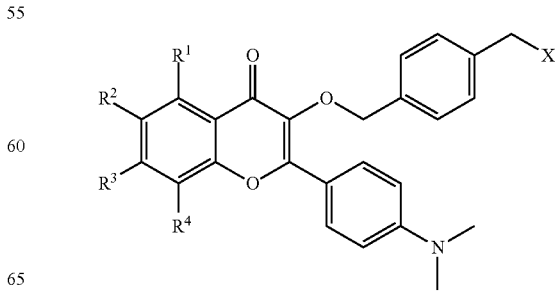

where each $R^1$-$R^4$ is individually an organic group or an hydrogen atom and X is a halogen atom; adding a zebrafish embryo to the embryo media; allowing the flavonoid compound to permeate into the zebrafish embryo; optionally allowing the zebrafish embryo to develop into a zebrafish larva; exciting the zebrafish embryo or optional zebrafish larva the with an excitation wavelength that excites the flavonoid and induces a fluorescence response; and capturing an image of the zebrafish embryo, the optional zebrafish larva, or both the zebrafish embryo and the optional zebrafish larva.

In a tenth embodiment, the present invention provides a method as in the ninth embodiment, where the zebrafish embryo is at from about 4 to about 170 hours post fertilization when it is added to the embryo media.

In an eleventh embodiment, the present invention provides a method as in either the ninth or tenth embodiments, where the embryo media is E3 media.

In a twelfth embodiment, the present invention provides a method as in any of the ninth through eleventh embodiments, where the zebrafish embryo includes a yolk syncytial layer and the flavonoid compound selectively stains the yolk syncytial layer.

In a thirteenth embodiment, the present invention provides a method as in any of the ninth through twelfth embodiments, where the excitation wavelength is from about 550 nm to about 570 nm or from about 400 nm to about 460 nm.

In a fourteenth embodiment, the present invention provides a method as in any of the ninth through thirteenth embodiments, where the zebrafish embryo develops into a zebrafish larva.

In a fifteenth embodiment, the present invention provides a method as in any of the ninth through fourteenth embodiments, where each R of the flavonoid is individually an alkyl group or a hydrogen atom.

In a sixteenth embodiment, the present invention provides a method as in any of the ninth through fifteenth embodiments, where the flavonoid compound is defined by the formula

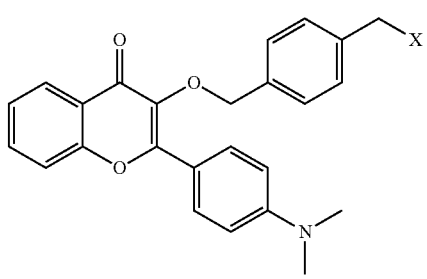

where X is a halogen atom.

In a seventeenth embodiment, the present invention provides a method as in any of the ninth through sixteenth embodiments, where the flavonoid compound is defined by the formula

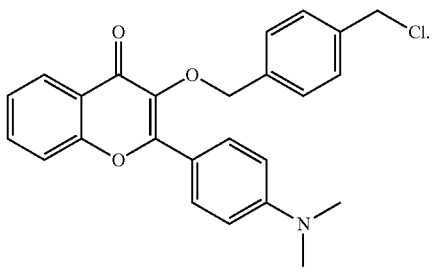 [SMILES: CN(C)c1ccc(-c2oc3ccccc3c(=O)c2OCc2ccc(CCl)cc2)cc1]

In an eighteenth embodiment, the present invention provides a method of detecting proteins comprising: adding a flavonoid compound to a sample solution, where the flavonoid compound is defined by the formula

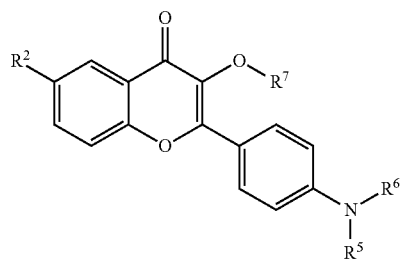

where R2 is an organic group or an hydrogen atom, each R5 and R6 is individually an organic group or an hydrogen atom or where R5 and R6 combine to form a single organic group, and R7 is an organic group or an hydrogen atom; exciting the sample solution with an excitation wavelength that induces a fluorescence response if the flavonoid compound is bound to a protein; and determining the fluorescence response, where a fluorescence response indicates the presence of protein in the sample solution, and no significant fluorescence response indicates the lack of protein in the sample solution.

In a nineteenth embodiment, the present invention provides a method as in the eighteenth embodiment, where the sample solution includes SDS-PAGE.

In a twentieth embodiment, the present invention provides a method as in either the eighteenth or nineteenth embodiments, where the sample solution includes an SDS-PAGE gel.

In a twenty-first embodiment, the present invention provides a method as in any of the eighteenth through twentieth embodiments, where the flavonoid compound selective binds to albumin proteins.

In a twenty-second embodiment, the present invention provides a method as in any of the eighteenth through twenty-first embodiments, where the flavonoid compound is selected from the group consisting of

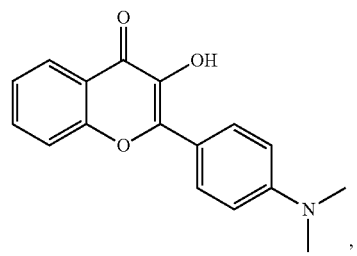

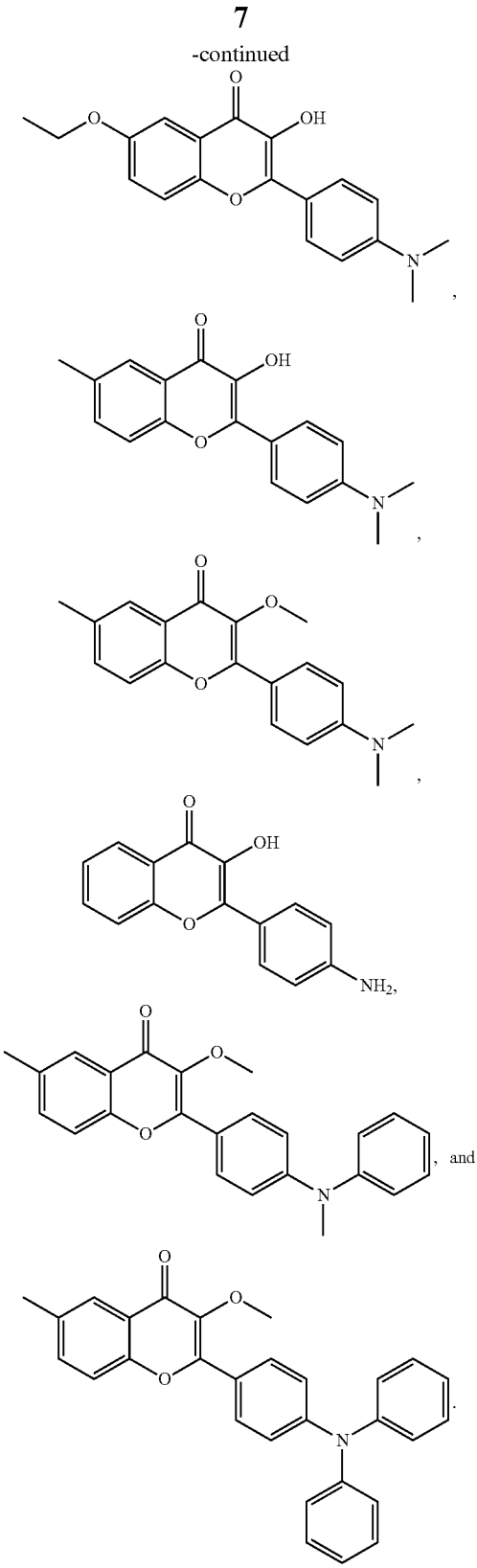

In a twenty-third embodiment, the present invention provides a method of imaging zebrafish blood vessels comprising providing an embryo media; adding a flavonoid compound to the embryo media, where the flavonoid compound is defined by the formula where each R1-R4 is individually an organic group or a hydrogen atom, each $R^5$ and $R^6$ is individually an organic group or a hydrogen atom or where R5 and R6 combine to form a single organic group, and R7 is an organic group; adding a zebrafish of about 72 to about 108 hours post fertilization to the embryo media; allowing the flavonoid compound to permeate into the zebrafish; exciting the zebrafish with an excitation wavelength that excites the flavonoid and induces a fluorescence response; and capturing an image of the zebrafish.

In a twenty-fourth embodiment, the present invention provides a method as in the twenty-third embodiment, where the step of allowing the flavonoid compound to permeate into the zebrafish takes from about 6 to about 8 hours.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 10:
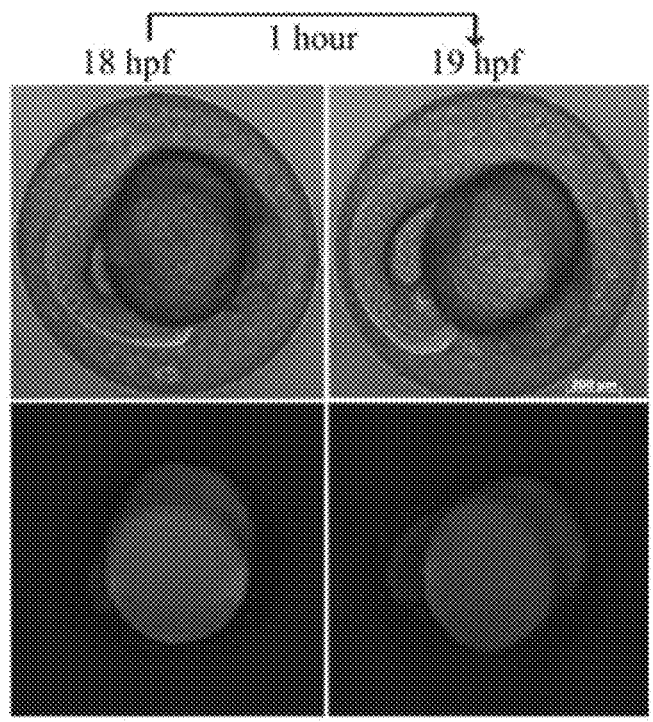
Figure 11:
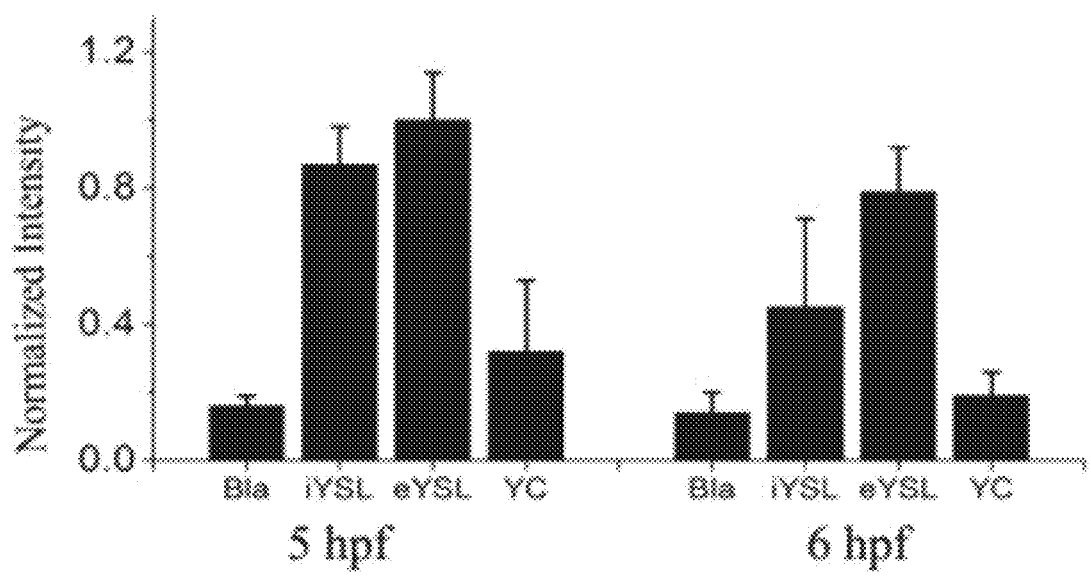
Figure 12:
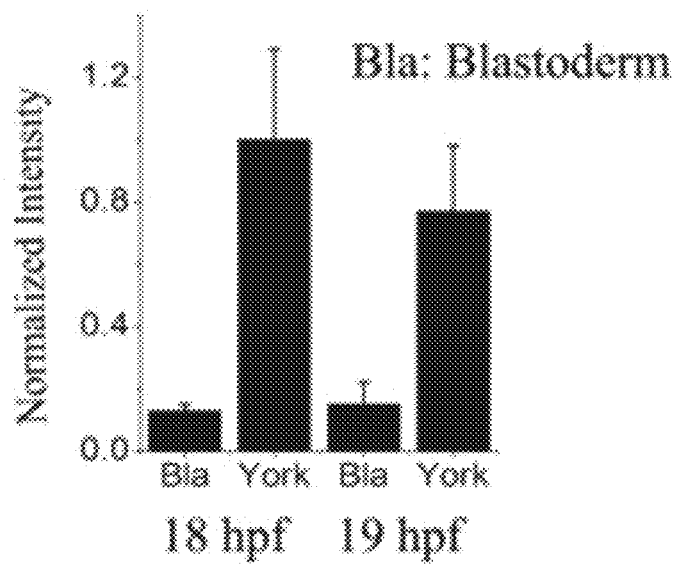
Figure 13:
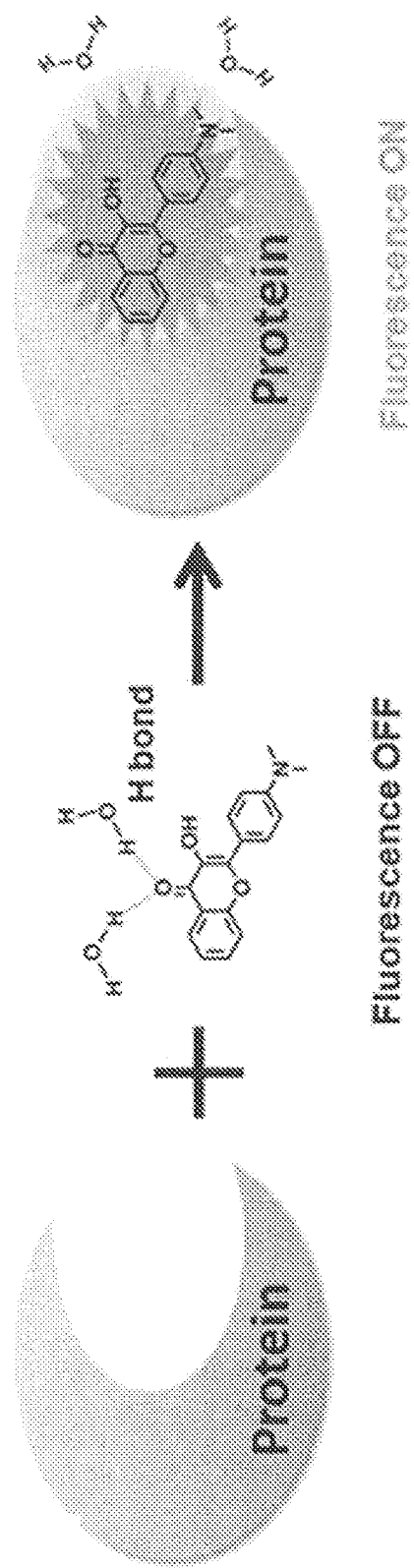
Figure 14:
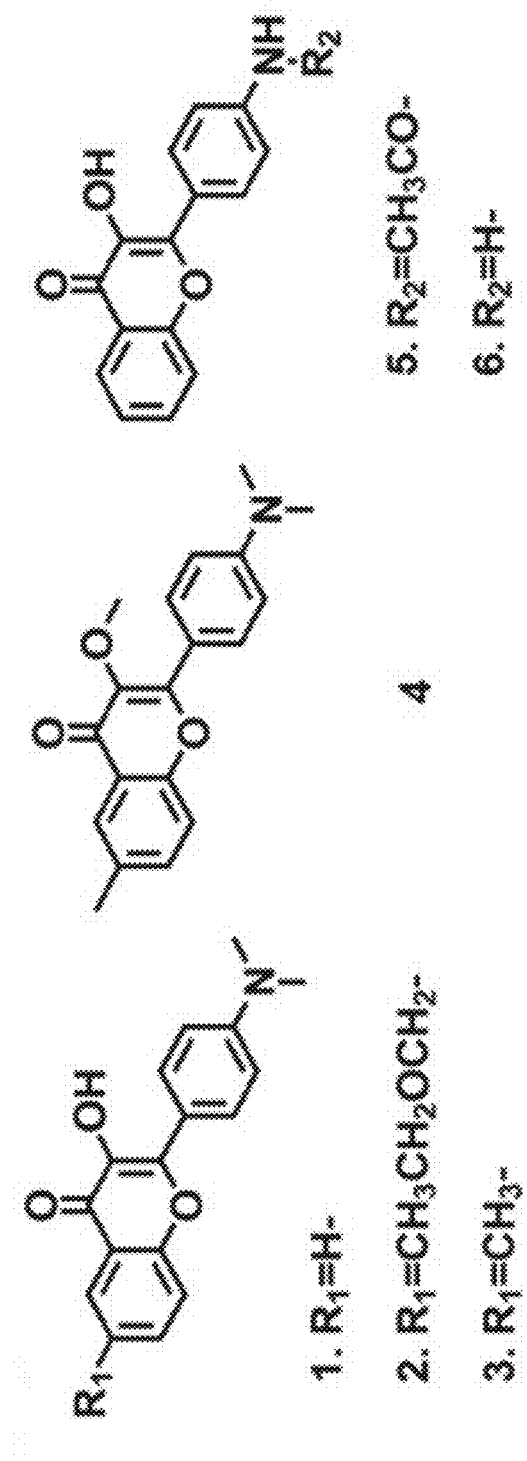
Figure 15:
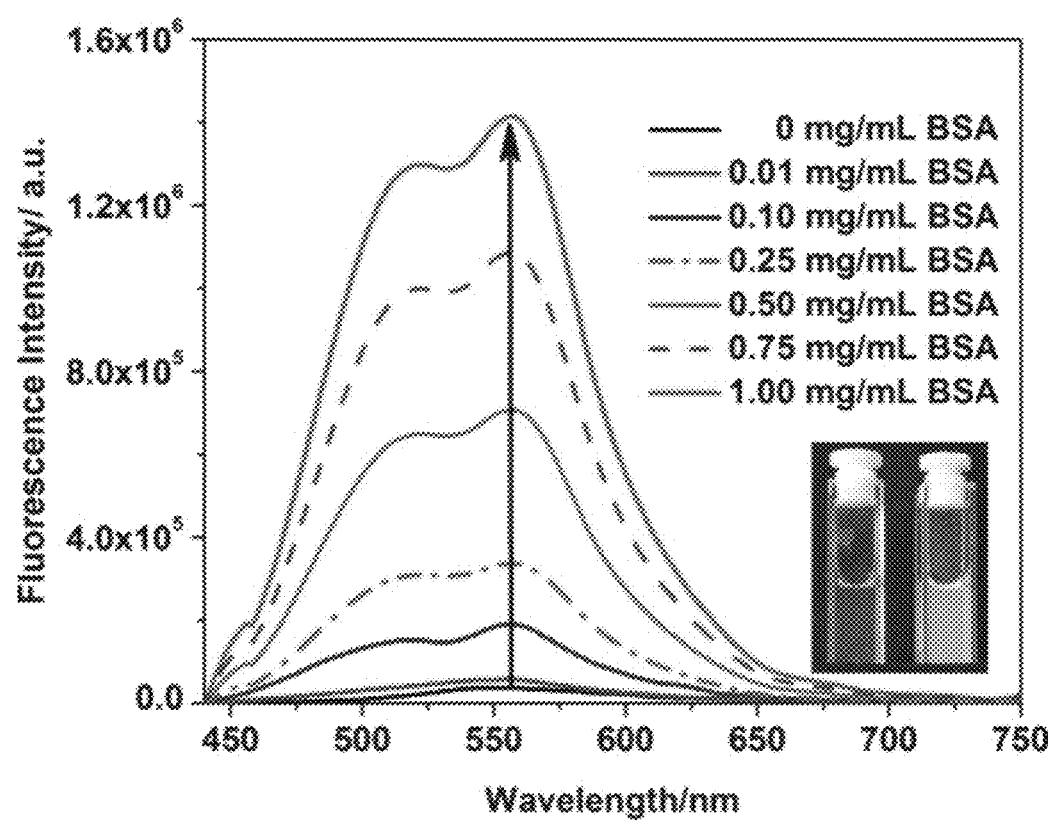
Figure 16:
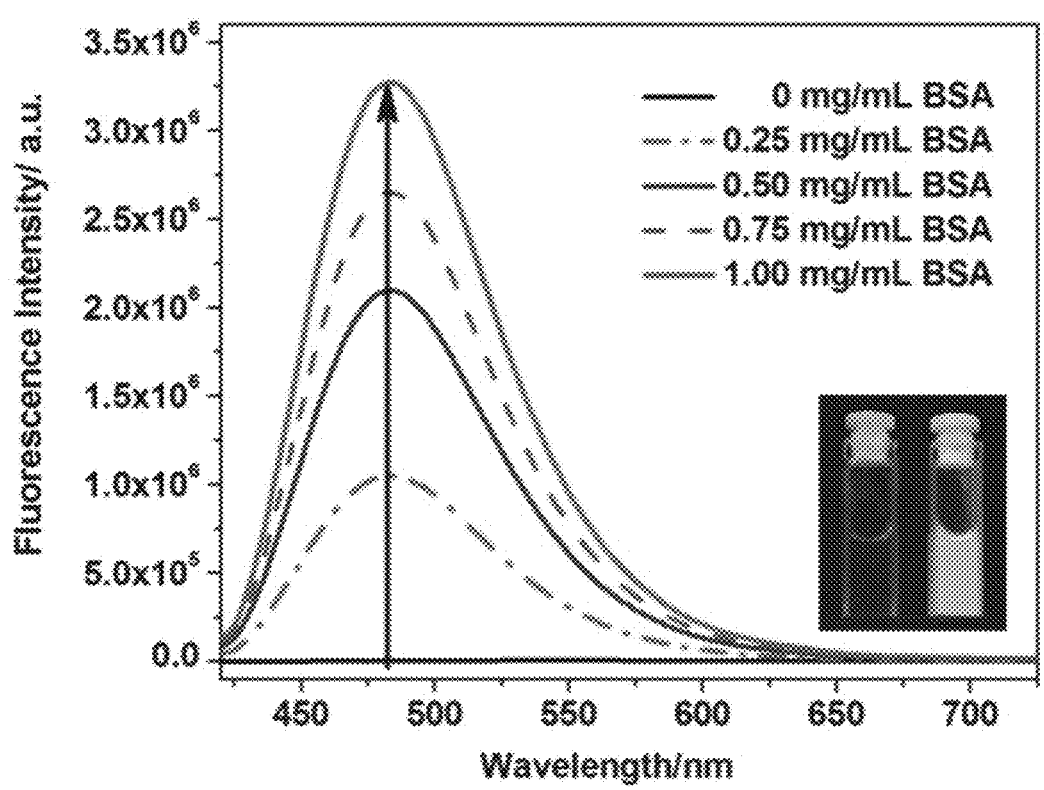
Figure 17:
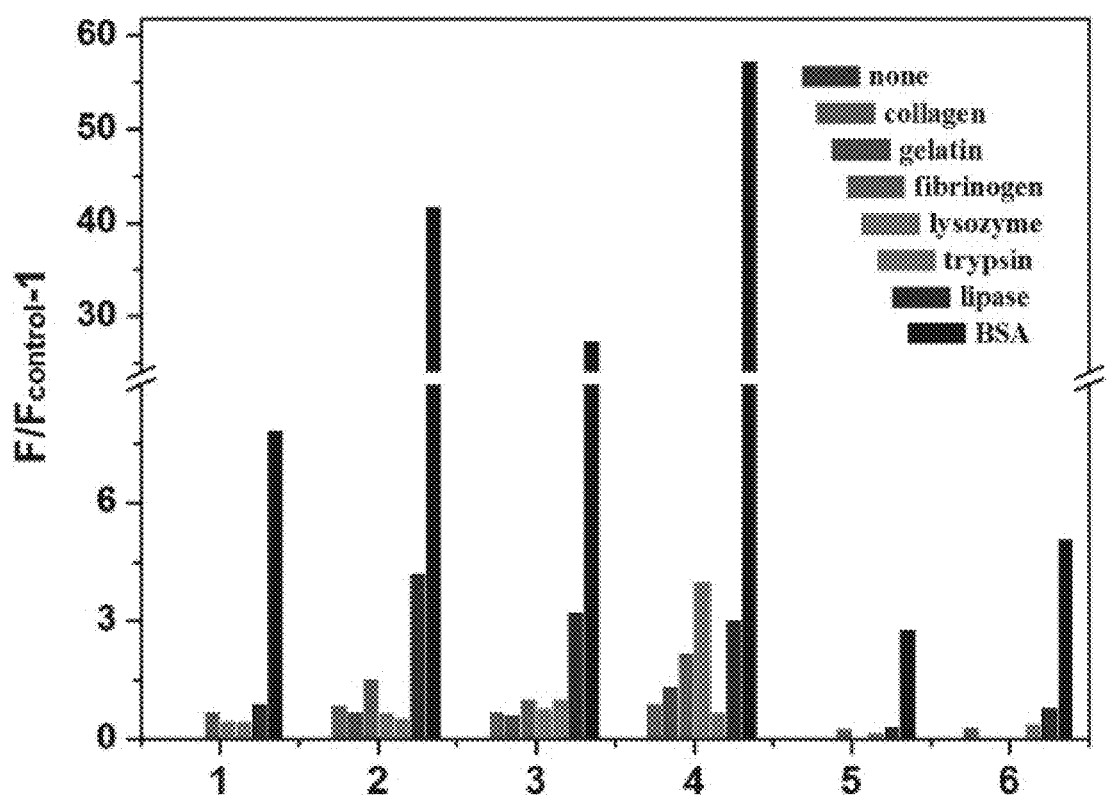
Figure 18:
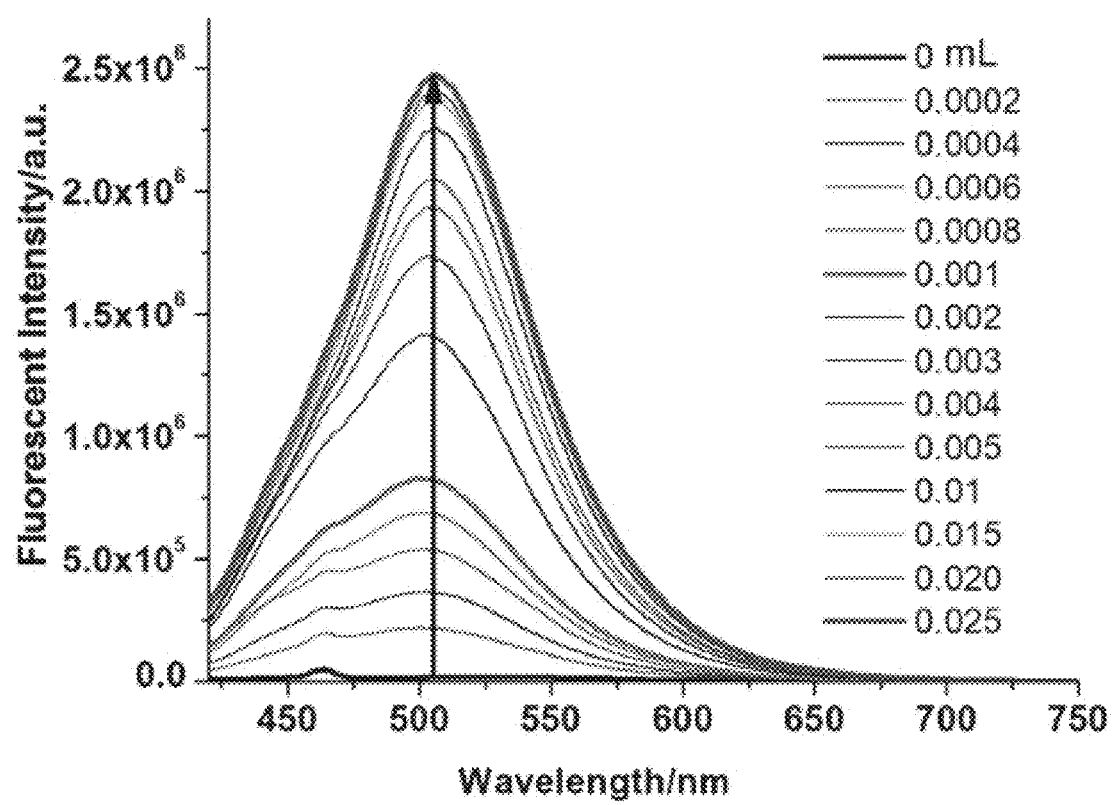
Figure 19:
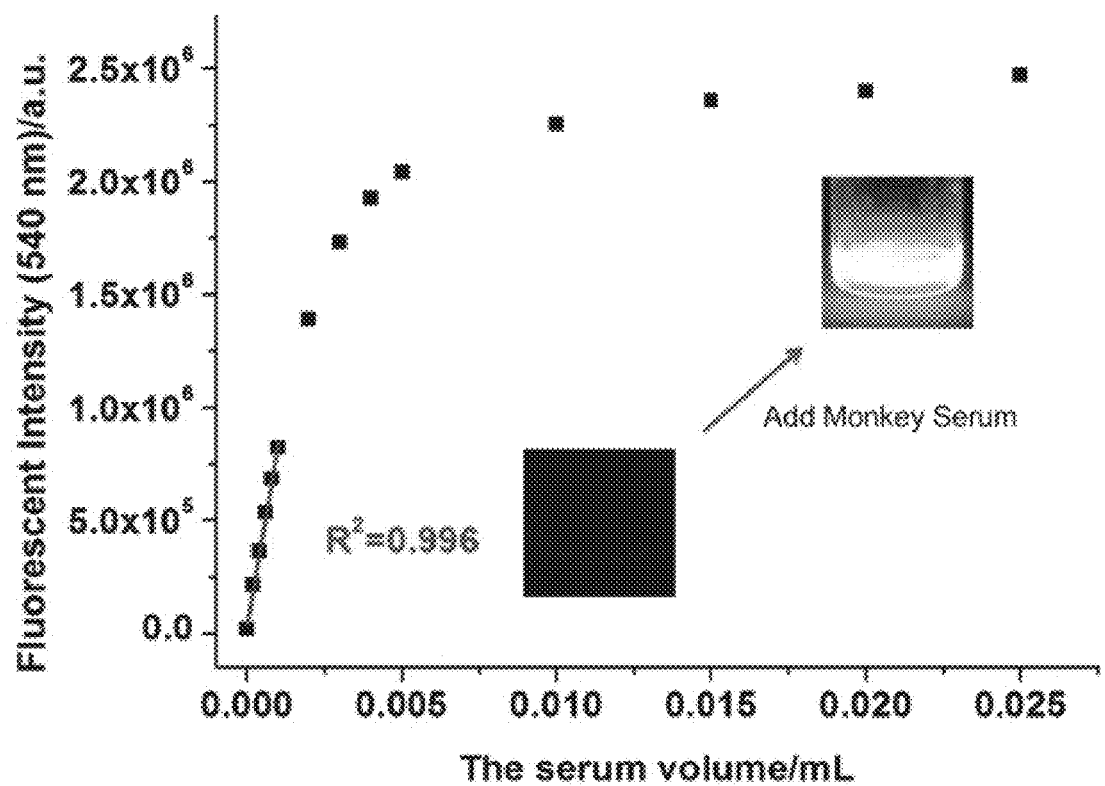
Figure 20:
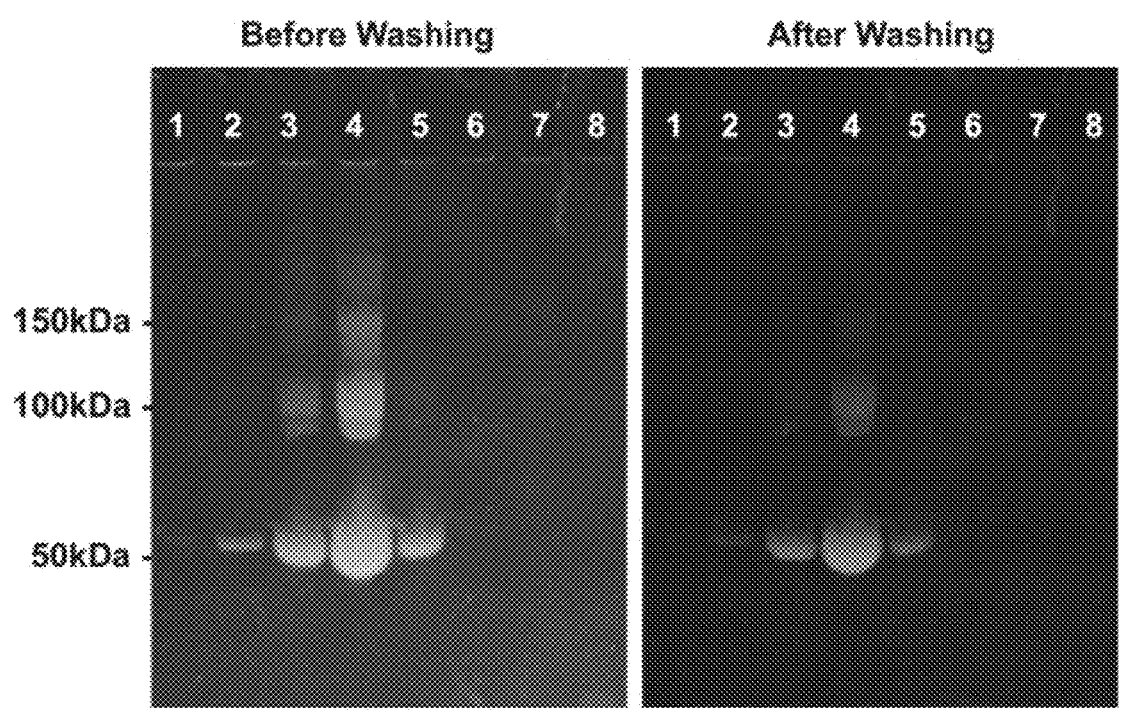
Figure 21:
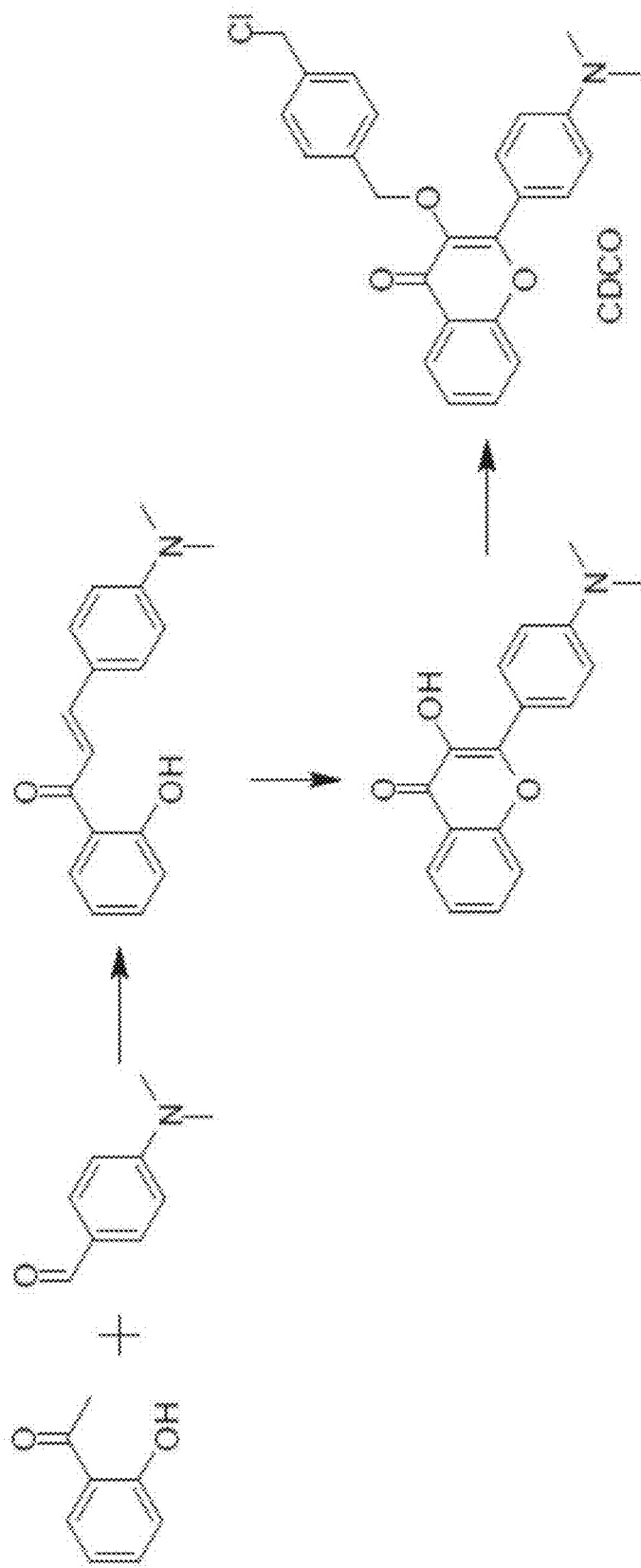
Figure 22:
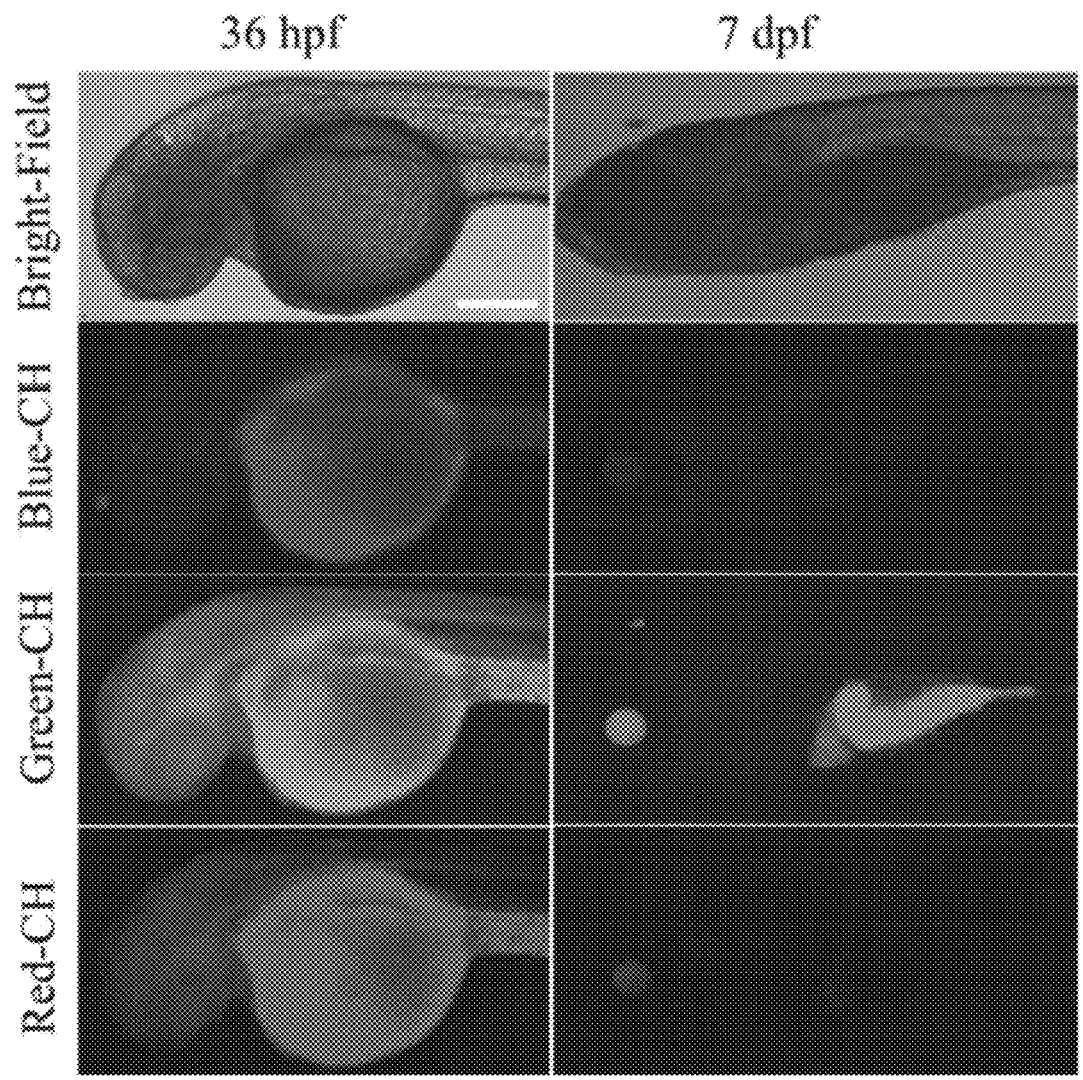
Figure 23:
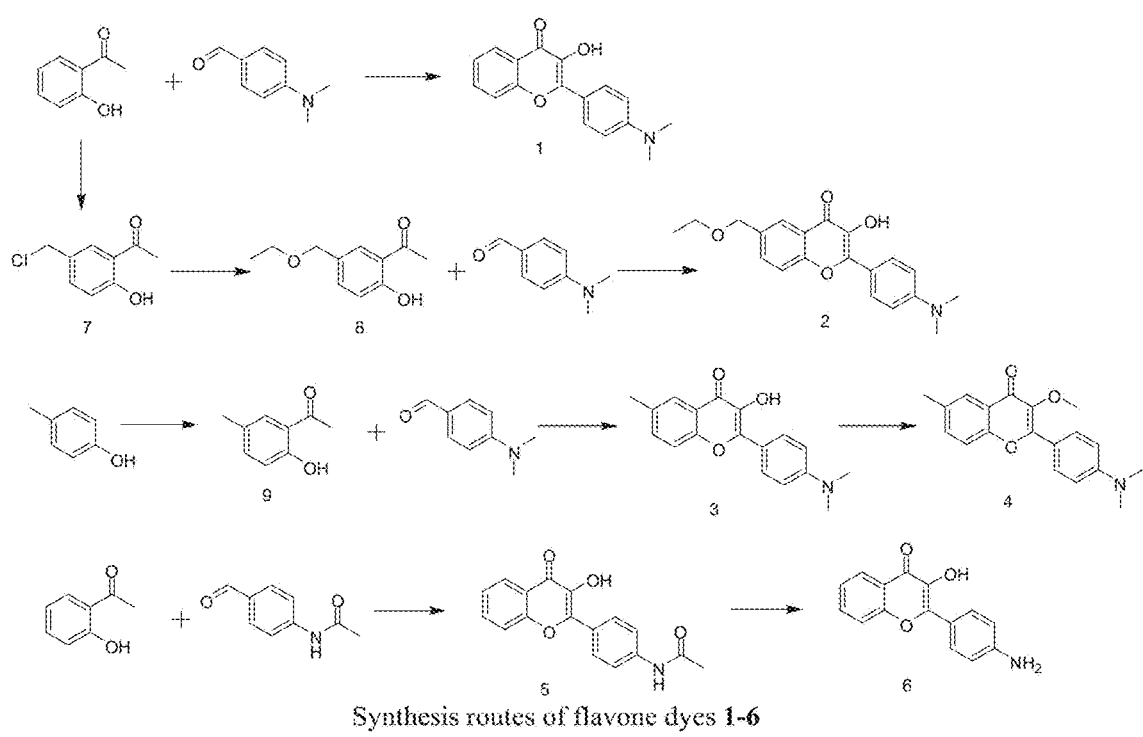

then the bright-field and red fluorescence images (right) were recorded by fluorescence microscope;

FIG. 10 is an image of the fluorescence stability and leakage of CDCO in zebrafish embryos. After 0.5 hour treatment of CDCO. The bright•field and red fluorescence images (left) of 18 hpf zebrafish embryo. This embryo was washed and incubated in E3 medium for 1 hour at 28.5° C. then the bright-field and red fluorescence images (right) were recorded by fluorescence microscope;

FIG. 11 is a chart showing the normalized red fluorescence intensities of at different embryo tissues;

FIG. 12 is a chart showing the normalized red fluorescence intensities of at different embryo tissues;

FIG. 13 is an illustration of the fluorescence turn-on for selective protein detection for one or more embodiments;

FIG. 14 provides the chemical structure of one or more embodiments of flavone dyes;

FIG. 15 provides a graph of the fluorescence spectra changes of flavone derivatives 1(a);

FIG. 16 provides a graph of the fluorescence spectra changes of flavone derivatives 4;

FIG. 17 provides the fluorescence enhancements ($F/F_{control}-1$) of compounds 1-6 (10 μM, 10 mM PBS buffer containing 0.5% DMSO, pH=7.4) in the absence and the presence of 0.1 mg/ml of various proteins;

FIG. 18 provides a chart of fluorescence spectra changes and of compound 4 (10 μM, in 1 mL of PBS buffer solution) upon addition of different volume of monkey serum;

FIG. 19 provides a chart of fluorescent intensities (λ=505 nm) of compound 4 (10 μM, in 1 mL of PBS buffer solution) upon addition of different volume of monkey serum;

FIG. 20 provides fluorescence images of several proteins in electrophoresis gel stained by compound 4 before and after washing 1. BSA at 0.1 μg; 2. BSA at 1 μg; 3. BSA at 10 μg; 4. BSA at 100 μg; 5. HSA at 10 μg; 6. Fibrinogen at 10 μg; 7. Lysozyme at 10 μg; 8. Trypsin at 10 μg;

FIG. 21 provides a synthesis scheme for one or more embodiments;

FIG. 22 provides an image of the fluorescence labeling of CDCO for the 36 hpf embryos and 7 hpf zebrafish larvae. The bright-field, blue-CH, green-CH, and red-CH images were captured by fluorescence microscopy. Blue-CH (Ex: 365 nm, Em: 420-470 nm), Green-CH (Ex: 450-490 nm, Em: 515-565 nm), and Red-CH (Ex: 575-600 nm, Em:612-682 nm). Exposure time: 100 ms. Scale bar: 200 nm.; and FIG. 23 provides chemical synthesis routes for flavone dyes 1-6.

DETAILED DESCRIPTION OF ILLUSTRATIVE EMBODIMENTS

Embodiments are based, at least in part, on the discovery that flavonoid compounds may be used as detection and imagining compounds. A flavonoid compound may be prepared to be selective for a protein, a portion or a living cell, or a portion of an organism. Advantageously, the flavonoid only provides a fluorescent response when excited at certain wavelengths if it is selectively bound. If the flavonoid is not selectively bound no fluorescence response or no significant fluorescence response will be emitted when the flavonoid is irradiated. No significant fluorescence response refers to a fluorescence response that is not significantly higher than the background.

In one or more embodiments, the flavonoid has an excitation wavelength of about 550 nm to about 570, which results in a fluorescence emission of about 585 nm to about 625 nm. In these or other embodiments, the flavonoid has an excitation wavelength of about 400 nm to about 460, which results in a fluorescence emission of about 500 nm to about 550 nm.

As an important natural pigment, flavonoids constitute a major portion of natural products present in fruits and vegetables, and are responsible for the colors (e.g. red and orange) in fruits and vegetables. A flavonoid-rich diet may provide protection against cardiovascular diseases and some forms of cancer. Flavonoid base compounds may provide molecular imaging reagents of low toxicity, which is desirable for imaging in living organisms.

In one or more embodiments, a flavonoid compound defined by the formula

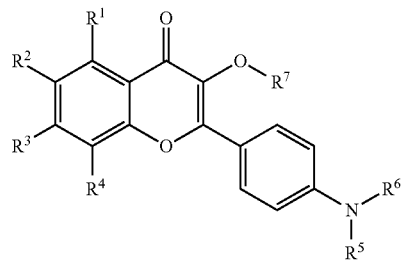

where each $R^1$-$R^4$ is individually an organic group or an hydrogen atom, each $R^5$ and $R^6$ is individually organic group or an hydrogen atom or where $R^5$ and $R^6$ combine to form a single organic group, and $R^7$ is an organic group or an hydrogen atom. In certain embodiments, $R^7$ is an organic group.

Suitable organic groups include hydrocarbon groups such as aliphatic hydrocarbon groups, cyclic hydrocarbon groups, aromatic hydrocarbon groups, and groups comprising combinations thereof. The organic groups may also include a heteroatoms replacing a carbon in a hydrocarbon structure. Specific heteroatoms include oxygen, sulfur, and nitrogen. The organic group may also include halogen atoms. Specific examples of halogen atoms include fluorine, chlorine, bromine, and iodine. In these or other embodiments, the organic group may be an alkyl group. Suitable alkyl groups include linear branched or alkyls. Specific examples of alkyl groups include methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl. In these or other embodiments, the organic group may include a cycloalkyl or an aromatic group.

Flavonoid compounds may be used to image an organism. In one or more embodiments, the method of imaging an organism comprises combining an organism with at least one cell and a flavonoid compound and allowing the flavonoid compound to permeate into the organism. If the flavonoid compound selectively binds to the organism it will emit a fluorescence emission when suitably excited. Thus, irradiating the organism with an excitation wavelength that excites the flavonoid and induces a fluorescence response, and an image of the organism may be captured.

Flavonoid compounds may be used to image zebrafish embryos. In one or more embodiments, the method of imaging a zebrafish embryo comprises providing an embryo media, adding a flavonoid compound to the embryo media, adding a zebrafish embryo to the embryo media, allowing the flavonoid compound to permeate into the zebrafish embryo; optionally allowing the zebrafish embryo to develop into a zebrafish larva, exciting the zebrafish embryo or optional zebrafish larva the with an excitation wavelength that excites the flavonoid and induces a fluorescence response, and capturing an image of the zebrafish embryo, the optional zebrafish larva, or both the zebrafish embryo and the optional zebrafish larva. In certain embodiments, the zebrafish embryo develops into a zebrafish larva.

Those skilled in the art will recognize that a zebrafish embryo includes a yolk syncytial layer. Advantageously, the flavonoid compound may selectively stain the yolk syncytial layer. It has been found that flavonoid dyes may selectively bind to albumin proteins. Because of the selective binding of the flavonoid compounds, they may be used to track and study the growth and development of a zebrafish, which involves the yolk syncytial layer.

Zebrafish embryo media is a solution that suitable for storing zebrafish embryos or allowing zebrafish embryos to develop. A suitable zebrafish embryo media is E3 media. E3 media may include 15 mM NaCl, 0.5 mM KCl, 1 mM $MgSO_4$, 1 mM $CaCl_2$, 0.15 mM $KH_2PO_4$, 0.05 mM $Na_2HPO_4$, 0.7 mM $NaHCO_3$, $10^{-5}$% methylene blue; at pH 7.5.

In one or more embodiments, the concentration of the flavone compound suitable for imaging zebrafish embryos may be from about 1 μM to about 50 μM, in other embodiments from about 3 μM to about 25 μM, and in other embodiments from about 6 μM to about 15 μM.

In one or more embodiments, the zebrafish embryo maybe prepared in the zebrafish embryo media. In these embodiments, fertilization takes place in the zebrafish embryo media. In other embodiments, the zebrafish embryo may be transferred to the zebrafish embryo media post fertilization. In these or other embodiments, zebrafish embryo is added to the embryo media from about 4 to about 170 hours post fertilization, in other embodiments from about 6 to about 120 hours post fertilization, and in other embodiments from about 8 to about 80 hours post fertilization.

In one or more embodiments, flavonoid compounds suitable for use for imaging zebrafish embryos may be defined by the formula

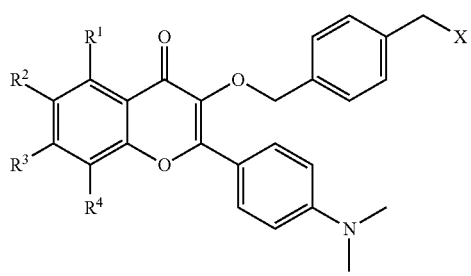

where each $R^1$-$R^4$ is individually an organic group or an hydrogen atom and X is a halogen atom. In these or other embodiments, each R of the flavonoid is individually an alkyl group or a hydrogen atom.

In certain embodiments, the flavonoid compounds suitable for use for imaging zebrafish embryos may be defined by the formula

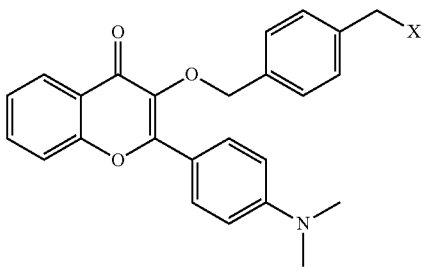

where X is a halogen atom.

In certain embodiments, the flavonoid compounds suitable for use for imaging zebrafish embryos may be defined by the formula

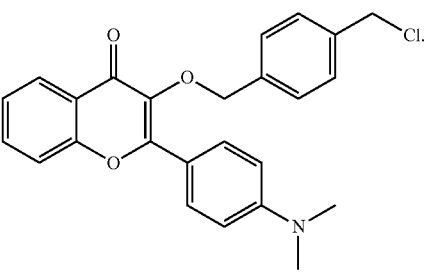 [SMILES: CN(C)c1ccc(-c2oc3ccccc3c(=O)c2OCc2ccc(CCl)cc2)cc1]

Flavonoid compounds may be used to image zebrafish blood vessels. In one or more embodiments, the method of imaging zebrafish blood vessels comprises providing an embryo media; adding a flavonoid compound to the embryo media, adding a zebrafish of about 72 to about 108 hours post fertilization to the embryo media; allowing the flavonoid compound to permeate into the zebrafish; exciting the zebrafish with an excitation wavelength that excites the flavonoid and induces a fluorescence response; and capturing an image of the zebrafish.

The flavonoid compound may be allowed to permeate into the zebrafish for a sufficient amount of time prior to imaging. In one or more embodiments, the flavonoid compound may be allowed to permeate into the zebrafish from about 1 hours to about 15 hours, in other embodiments from about 3 hours to about 12 hours, and in other embodiments about 6 hours to about 8 hours.

In one or more embodiments, the concentration of the flavone compound suitable for imaging zebrafish blood vessels may be from about 1 μM to about 50 μM, in other embodiments from about 3 μM to about 25 μM, and in other embodiments from about 6 μM to about 15 μM.

In one or more embodiments, flavonoid compounds suitable for use for imaging zebrafish blood vessels is defined by the formula

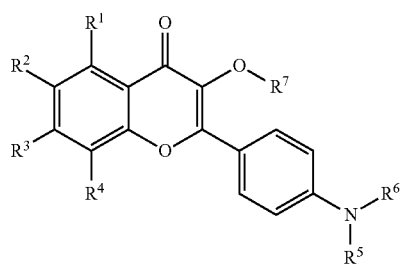

where each R1-R4 is individually an organic group or an hydrogen atom, each R5 and R6 is individually organic group or an hydrogen atom or where R5 and R6 combine to form a single organic group, and R7 is an organic group or an hydrogen atom.

In one or more embodiments, flavonoid compounds suitable for imaging zebrafish blood vessels may be selected from

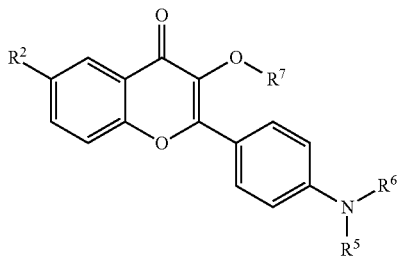

where $R^2$ and $R^7$ are individually selected from alkyl groups, and $R^5$ and $R^6$ are individually selected from alkyl or aromatic groups. In certain embodiments, $R^2$ and $R^7$ are individually selected branched or linear alkyl groups.

Flavonoid compounds may be used to detect proteins. Due to the flavones ability to fluoresce when selectively bound, proteins may be detected without requiring a "wash out step," or removing the excess flavone. In one or more embodiments, the method of detecting proteins comprises adding a flavonoid compound to a sample solution exciting the sample solution with an excitation wavelength that induces a fluorescence response if the flavonoid compound is bound to a protein; and determining the fluorescence response, where a fluorescence response indicates the presence of protein in the sample solution, and no significant fluorescence response indicates the lack of protein in the sample solution.

A sample solution is a solution that may contain protein. The sample solution may contain insoluble such as polymers or other gels. For example the sample solution may contain a polyacrylamide gel. In these or other embodiments, the protein to be detected may be in the gel. In certain embodiments, the gel may be used for or have been used in electrophoresis. In certain embodiments, gel electrophoresis on a solution that may contain protein may take place, and then the gel may be moved to a solution with a flavone to detect protein. Advantageously, the flavone can detect protein in the presence of sodium dodecyl sulfate (SDS). In these or other embodiments, the samples solution may include an SDS page gel.

In certain embodiments, the flavone compound may be specific for the protein albumin.

In one or more embodiments, the concentration of the flavone compound suitable detecting proteins may be from about 0.1 mM to about 50 mM, in other embodiments from about 1 mM to about 25 mM, and in other embodiments from about 5 mM to about 15 mM.

In one or more embodiments, flavonoid compounds suitable for detecting protein may be defined by the formula

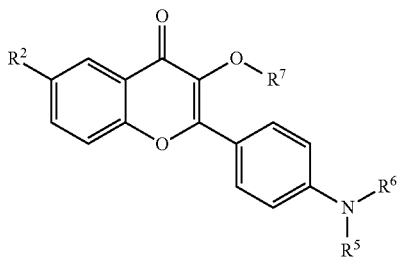

where $R^2$ is an organic group or an hydrogen atom, each $R^5$ and $R^6$ is individually an organic group or an hydrogen atom or where $R^5$ and $R^6$ combine to form a single organic group, and $R^7$ is an organic group or an hydrogen atom;

In one or more embodiments, flavonoid compounds suitable for detecting protein may be selected from

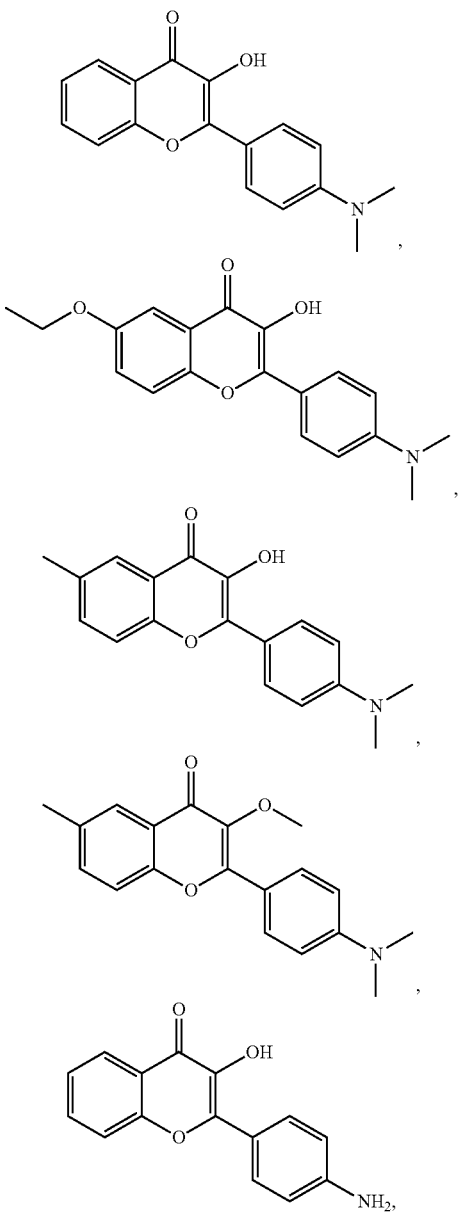

-continued

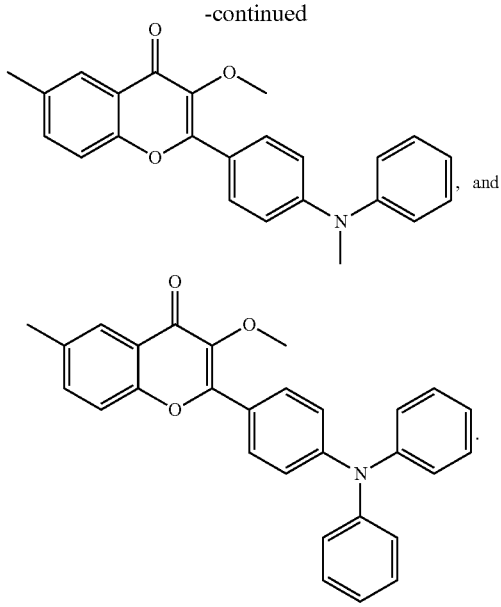
, and

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Preparing 3-(4-(chloromethyl)benzyloxy)-2-(4-(dimethylamino)phenyl)-4H-chromen-4-one (CDCO)

A scheme for the synthesis of CDCO is provided in FIG. 21.

Reagents and Instrumentation $^1$H NMR and $^{13}$C NMR spectra were obtained using an AVANCE II apparatus from Bruker Corporation (Billerica, Mass.). UV-vis spectra were acquired on an 8453 diode-array spectrometer from Hewlett-Packard (Palo Alto, Calif.). Fluorescence spectra were measured by RF-5301 PC spectrometer from Shimadzu Corporation (Kyoto, Japan). Electrospray ionization (ESI) mass spectra were acquired with a Synapt HDMS quadrupole/time-of-flight (Q/ToF) mass spectrometer from Waters Corporation (Milford, Mass.). All the solvents for the fluorescence experiments were analytic grade, which were purchased from Fisher Scientific (Waltham, Mass.) and used without further purification. Bovine serum albumin was purchased from Sigma Aldrich (St. Louis, Mo.). Zebrafish vitellogenin standard was purchased from Cayman Europe Biosense Laboratories (No. V01008301). The fluorescence imaging was obtained by X-Cite™ Series 120Q fluorescence microscope from Lumen Dynamics. For the blue channel filter: excitation 365 nm, beam splitter FT 395 nm, emission 445/50 nm. For the green channel filter: excitation 450-490 nm, beam splitter FT 510 nm, emission 515-565 nm. For the red channel filter: excitation 587/25 nm, beam splitter FT 605 nm, emission 647/70 nm.

(E)-3-(4-(dimethylamino)phenyl)-1-(2-hydroxyphenyl)prop-2-en-1-one 2-hydroxyacetophenone (10 mmol) was added to a solution of the 4-(dimethylamino)benzaldehyde (10 mmol) in ethanol (20 mL) and aqueous NaOH (4 g in 10 ml water). The mixture was stirred at 50° C. for 4 hours then at room temperature for another 10 hours. The reaction mixture was neutralized with 1M HCl. The solid precipitate was collected by filtration. The product was directly used for the next step without further purification.

2-(4-(dimethylamino)phenyl)-3-hydroxy-4H-chromen-4-one (E)-3-(4-(dimethyl amino)phenyl)-1-(2-hydroxyphenyl)prop-2-en-1-one (7 mmol) was dissolved in 25 mL ethanol and aqueous NaOH (3 g in 10 mL water). 4 mL of 30% $H_2O_2$ solution was slowly added into the reaction solution which was placed in an ice water bath. After stirring at room temperature for 10 hours, the mixture was poured into ice water and precipitate was collected and washed with ethanol. The product was purified by recrystallization from ethanol. Yield=59%. $^1$H NMR (d6-DMSO, 300 MHz): δ=8.22 (d, 2H), 8.06 (d, 1H), 7.71 (m, 2H), 7.41 (m, 1H), 6.8 (d, 2H).

3-(4-(chloromethyl)benzyloxy)-2-(4-(dimethylamino)phenyl)-4H-chromen-4-one (CDCO)

The powdered $K_2CO_3$ (3 mmol) was added into a solution of 1,4-bis(chloromethyl)benzene (4 mmol) in acetonitrile (25 mL), then 2-(4-(dimethylamino)phenyl)-3-hydroxy-4H-chromen-4-one (1 mmol) solved in 10 mL of acetonitrile was added dropwise. Reaction was stirred at 60° C. for 12 hours and was then filtered. The filtrate was evaporated to dryness via reduced pressure distillation. The crude product was purified by column chromatography (from $CH_2Cl_2$ to $CH_2Cl_2$: EtOAc=1:1) to provide the pure product. Yield=47%. $^1$H NMR (d6-DMSO, 300 MHz): δ=8.09 (d, 1H), 8.01 (d, 2H), 7.78 (m, 2H), 7.42 (m, 5H), 6.81 (d, 2H), 5.05 (s, 2H), 4.74 (s, 2H), 3.01 (s, 6H).
$^{13}$C NMR (75 MHz, $CDCl_3$): d=174.6, 156.9, 155.1, 151.2, 138.7, 137.5, 137.4, 137.1, 132.9, 130.2, 129.0, 128.4, 125.6, 124.4, 117.8, 111.9, 73.2, 46.1, 40.5. HRMS: m/z calculated for $C_{25}H_{22}ClNO_3$ (M+H)$^+$: 420.1366. found: 420.1441.

Bovin Serum Albumin (BSA)

The bovin serum albumin (BSA) as the common protein model was used to investigate the interaction between CDCO and proteins. After addition of one equivalent of BSA, the absorption peak at 385 nm was shifted to 402 nm. With the excitation at 400 nm, the fluorescence intensity of CDCO was enhanced about 2-fold, which was accompanied with a large blue-shift (by about 60 nm) from 560 nm to 500 nm. The observed blue-shift in fluorescence suggests that the CDCO dyes entered the BSA microenvironment of lower polarity. However, when the sample was excited at 570 nm, a red/near-infrared fluorescence peak was detected at 700 nm. In order to determine the location of CDCO on BSA, the displacement of CDCO was carried out by addition of warfarin, which is known to strongly bind to the warfarin binding site in Domain II A of BSA. However, addition of 5-fold excess of warfarin did not completely quench the red fluorescence, but shifted the emission to 750 nm. The observed spectral red-shift indicated that the interaction between CDCO and albumin might include another mode, in addition to the supermolecular effect as shown from other flavonoids. It is believed that the emission at 750 nm might be related to the complicated charge and energy transfer inside dye-BSA complex.

Thus, the above is a new near infrared (NIR)-emitting material useful in the transparent window of biological tissue (600-1000 nm). In addition, the probe exhibits no absorption overlap, which is of great importance for in vivo bioimaging.

Zebrafish at 16 Hours Post Fertilization (hpf)

Figure 1:
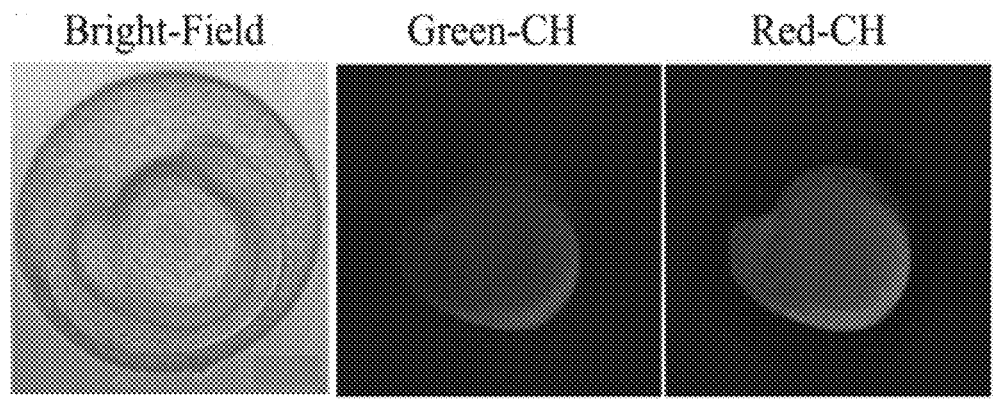
FIG. 1 provides an image of the bright-field. green-CH and red-CH images of the 16 hpf (14•somite stage in segmemation period) zebra fish embryo were captured by fluorescence microscopy.
Figure 2:
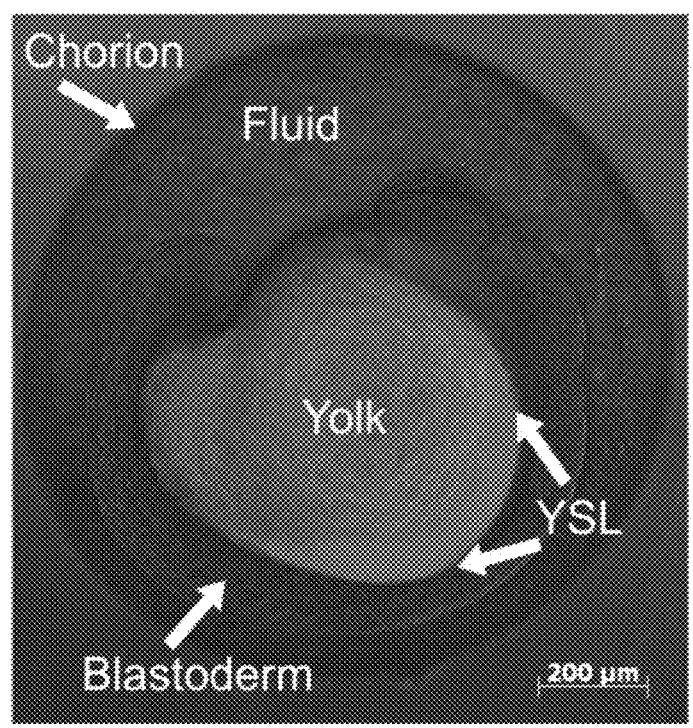
FIG. 2 provides an image of the red•merged image and tissues location of 16 hpf zebra fish embryo. Green-CH (Ex: 450-490 run, Em: 515-565 nm), and Red-CH (Ex: 575·600 nm. Em: 612-682 nm). Exposure time: 100 ms. Scale bar: 200 μm.
Figure 3:
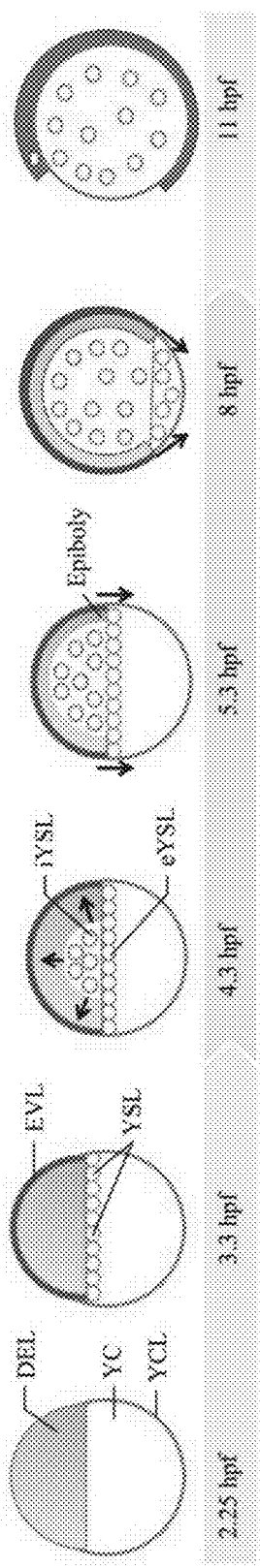
FIG. 3 is provides a schematic diagram of the distribution of YSL in early zebrafish development.
Figure 4:
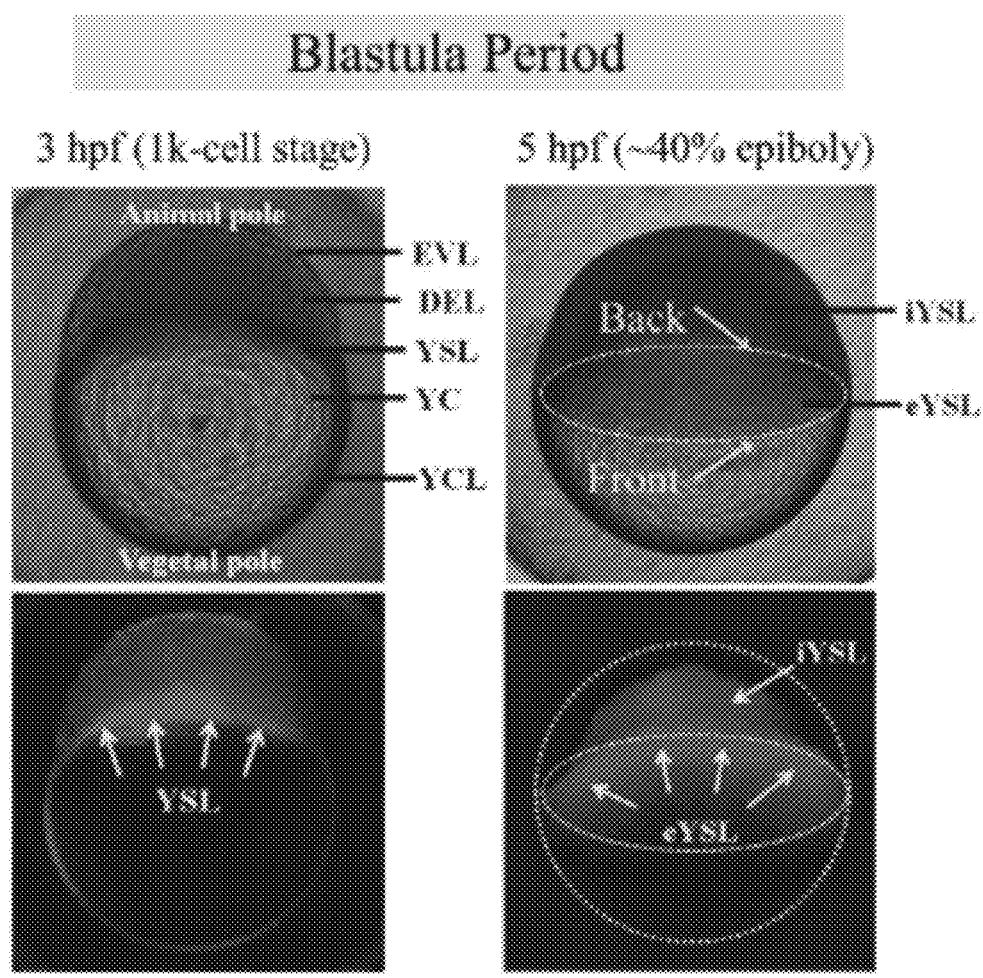
FIG. 4 provides an image of zebra fish embryos at the blastula period that were stained by 10 μM CDCO in E3 medium (0.2% DMSO) for 0.5 hour at 28.5° C.

Zebrafish embryos at 16 hours post fertilization (hpf) were initially used to study the CDCO's stain ability. A developing zebrafish body is normally covered by chorion and enveloping layer (EVL), which prevent dye molecules permeating into the fish body. In this example, 0.2% DMSO with 10 μM CDCO was infused to the E3 medium to decrease the barrier function of the zebra fish chorion without damaging the fish embryos' structural integrity. As shown in FIG. 1 and FIG. 2, after 30 minutes incubation with zebra fish embryos, CDCO successfully penetrated across the chorion and EVL of embryos, and then stained specifically the yolk-related region in the embryos. The sharp red image clearly indicated that the background signals from blastoderm and EVL region were kept at a minimum level, showing that the CDCO's interaction with other surrounding tissues was very weak. Study into the interaction between CDCO and zebrafish vitellogenin, which is the most abundant and representative protein in the yolk, revealed almost no red fluorescence. The junction between the yolk and blastoderm, as shown in FIG. 3, had brighter fluorescence. Thus, it is believed that CDCO selectively stained the YSL region.

Zebrafish at Various Stages of Post Fertilization

To investigate the location of CDCO labeling, zebra fish embryos at nine representative stages of early development were incubated with 10 μM CDCO for 30 minutes at 28.5° C., respectively (FIGS. 3-8). The YSL is initially generated by the collapse/fusion of marginal blastomeres with the yolk cell, and then a thin ring of YSL nuclei forms in front of blastoderm margin at high stage. Although the enveloping layer (EVL), deep layer cells (DEL), yolk cell (YC), and yolk cytoplasmic layer (YCL) all appeared partially stained, the YSL structure between the DEL and yolk cell can be clearly discriminated, revealing strong red fluorescence with the aid of CDCO, as shown in the left column of FIG. 4.

The yolk cell was barely stained, demonstrating the specific targeting of CDCO to the YSL instead of the yolk cell. During development, the YSL is subdivided into the external yolk syncytial layer (eYSL) and the internal yolk syncytial layer (iYSL). The eYSL located in front of the blastoderm margin and iYSL located below the blastoderm, are clearly visible at around 40% epiboly stage (about 5 hpf), as shown in the right column of FIG. 4.

Figure 5:
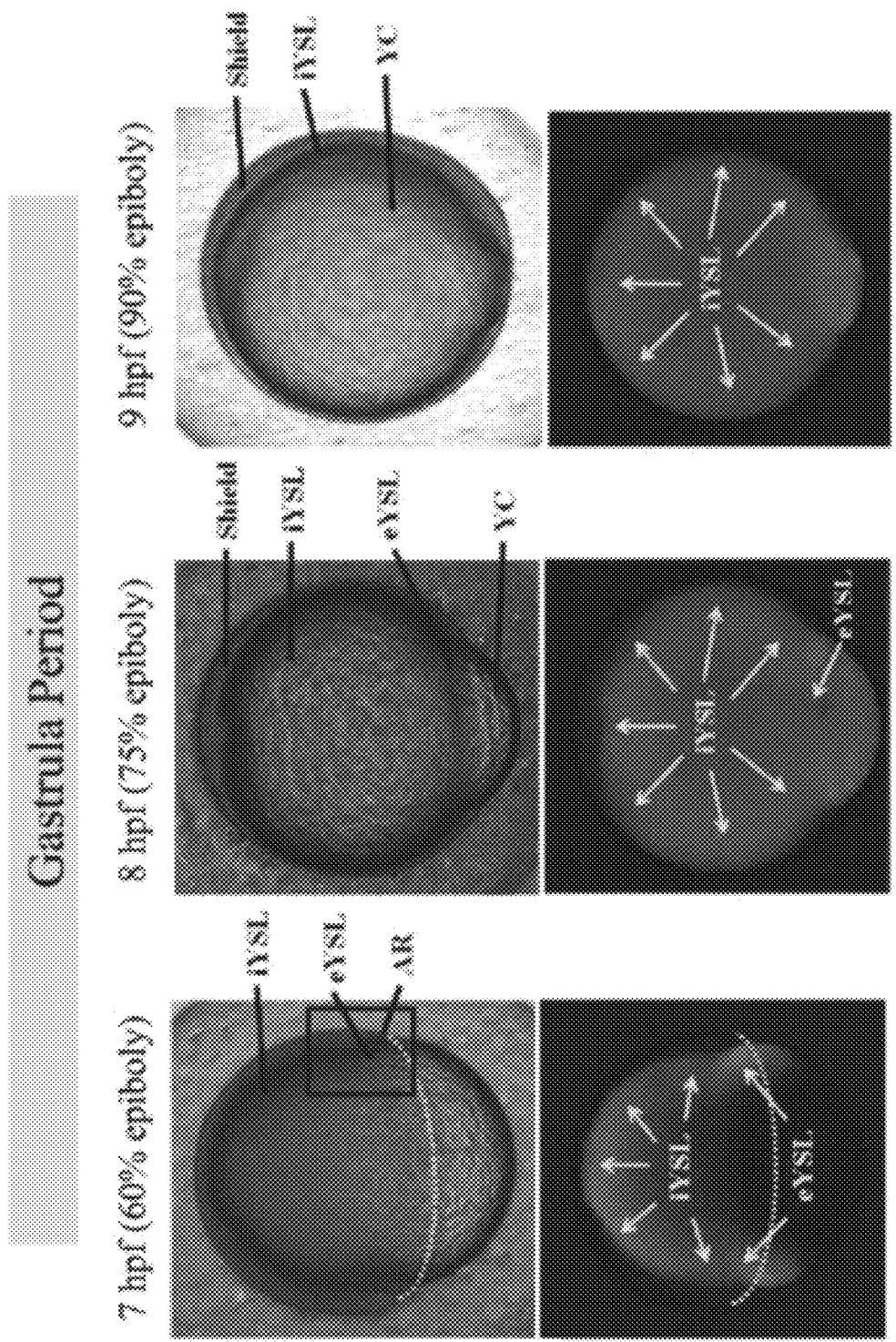
FIG. 5 provides an image of zebra fish embryos at the gastrula period that were stained by 10 μM CDCO in E3 medium (0.2% DMSO) for 0.5 hour at 28.5° C.
Figure 6:
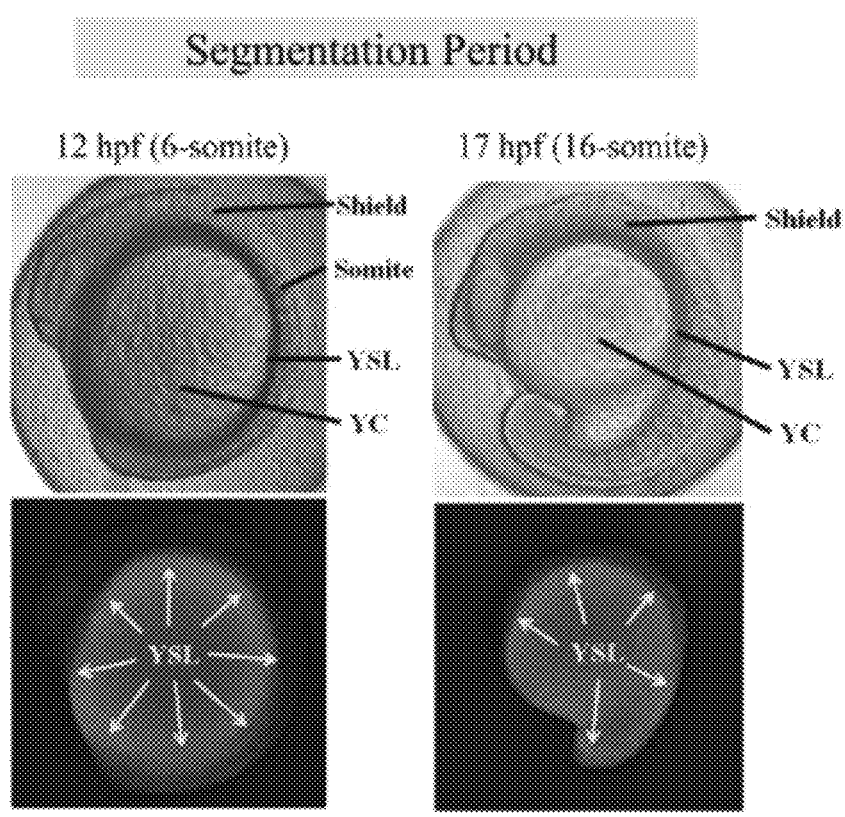
FIG. 6 provides an image of zebra fish embryos at the segmentation period that were stained by 10 μM CDCO in E3 medium (0.2% DMSO) for 0.5 hour at 28.5° C.
Figure 7:
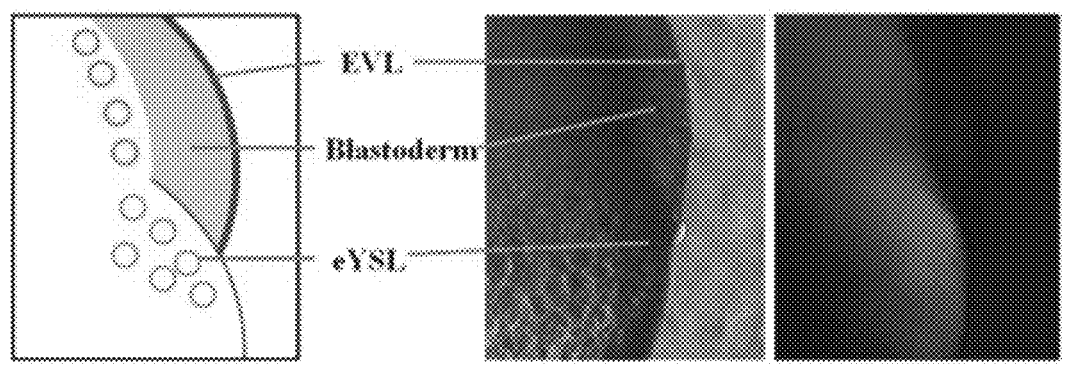
FIG. 7 is a schematic representation (left) of the distribution of YSL and enlarged fluorescence image (right) m shield region of 7 hpf embryo (boxed area)
Figure 8:
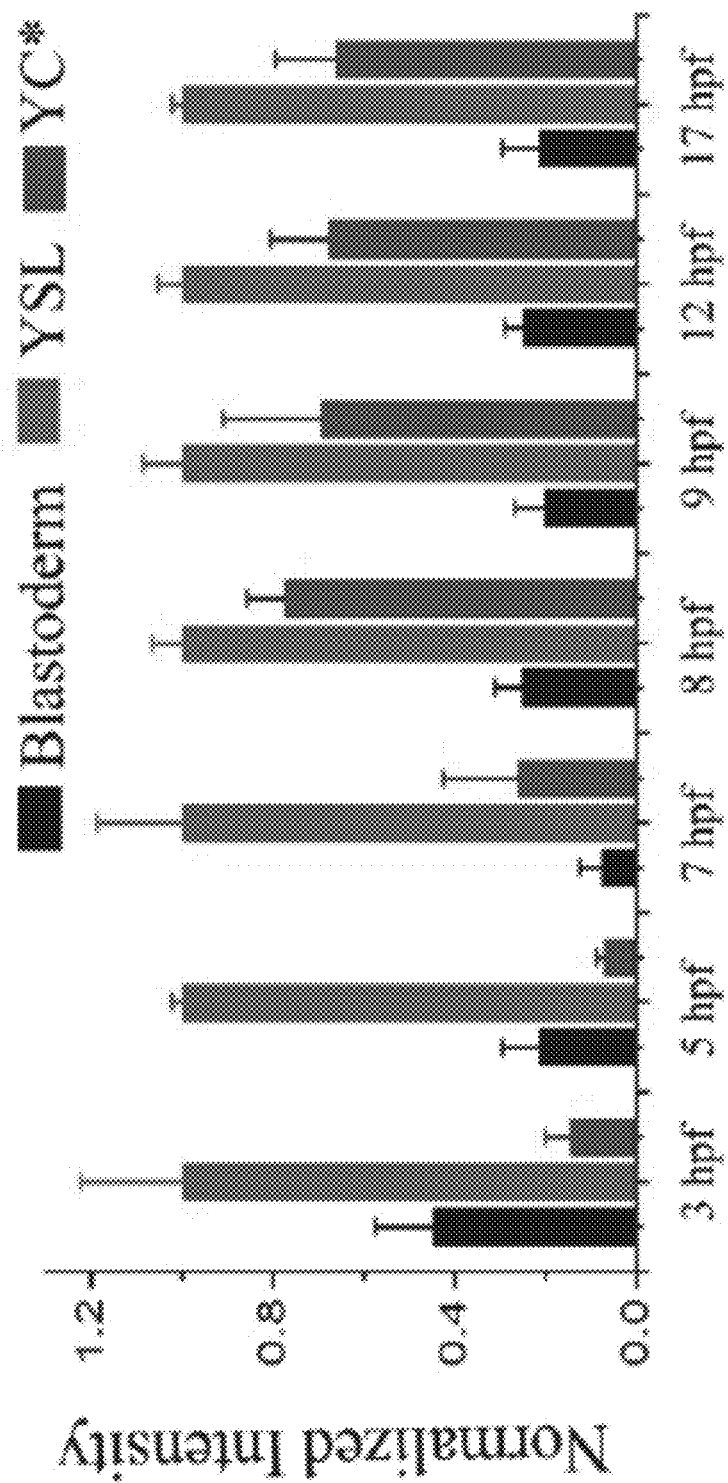
FIG. 8 is a chart of the fluorescence intensity in the middle of yolk. After 8 hour development, it is impossible to separate the YC and YSL, since the YC is mostly wrapped by YSL. Red-CH (Ex:575-600 nm. Em: 612-682 nm)
Figure 9:
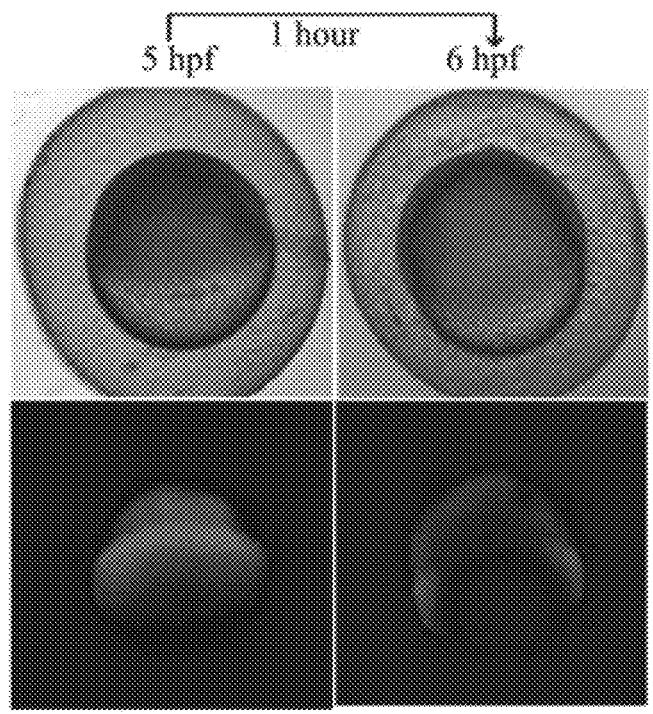
FIG. 9 is an image of the fluorescence stability and leakage of CDCO in zebrafish embryos. After 0.5 hour treatment of CDCO. The bright•field and red fluorescence Images (left) of 5 hpf zebrafish embryo. This embryo was washed and incubated in E3 medium for in hour at 28.5° C.

As shown in FIG. 5, as development proceeded of zebrafish embryos, the eYSL is predominantly driven by gastrulation movement and moves vegetally through the concerted actions of the yolk microtubules and cytoskeleton, as indicated by the red arrows in FIG. 5, around the actin ring (AR). The region where the eYSL meets the leading edge EVL cells associated with the epiboly process was clearly recognizable using this dye, as shown in FIG. 7. After the yolk cell was completely surrounded at early-segmentation period, as shown in FIG. 6, the red fluorescence intensity around the border line of yolk cell became much higher than the YC center, conforming with the location of the YSL. The CDCO was consistently confined to the YSL without significant leakage to the blastoderm, suggesting the strong interaction between CDCO and proteins in the YSL.

The YSL structure can persist on the edge of yolk cell until larval stages. For comparison, the 36 hpf embryos and 7 days old zebrafish larvae were incubated with CDCO for 1 hour, as shown in FIG. 22. The fluorescent labeling on the 36 hpf embryos displayed a strong red fluorescence as well as blue and green emission in the yolk region. However, for the 7 days old larval zebrafish in which the YSL had been completely absorbed, almost no red fluorescence was observed, while the green fluorescence was visible from intestinal lumen due to the CDCO swallowed by the zebrafish. This YSL-imaging method can selectively stain the YSL structure from its initial formation, to the dynamic epiboly, and finally to the disappearance of YSL, thus representing a promising tracking agent for zebrafish embryonic development studies.

Stability is one of the most important criteria for developing fluorescent imaging agents for living organisms, especially for tracking highly dynamic structures like the YSL. To demonstrate CDCO stability in labeling the YSL, zebrafish embryos at 5 hpf and 18 hpf were stained with 10 μM CDCO for 30 min. at 28.5° C., then washed several times with E3 medium and subsequently incubated for another 1 hour in the E3 medium.

As shown in FIGS. 9-12, after 1 hour incubation without further dyeing, no significant fluorescence leakage to blastoderm or somite was observed, indicating strong and consistent affinity of the CDCO to the YSL. In the experiments herein, CDCO showed almost no apparent toxicity since all the labeled embryos had similar morphology and size as non-labeled control ones from the same breeding, and a subset of the labeled embryos were raised to adult. The stable and biocompatible staining property of CDCO enables a long-term visualization method for tracking the development and migration of the YSL.

Zebrafish Info

Wild-type zebrafish embryos were collected and maintained as described in The Zebrafish Book by Monte Westerfield, which is incorporated herein by reference. Zebrafish were kept at 28.5° C. and maintained in E3 embryo medium (15 mM NaCl, 0.5 mM KCl, 1 mM $MgSO_4$, 1 mM $CaCl_2$, 0.15 mM $KH_2PO_4$, 0.05 mM $Na_2HPO_4$, 0.7 mM $NaHCO_3$, $10^{-5}$% methylene blue; pH 7.5).

For the example represented by FIGS. 1 and 2, 10 μL CDCO stock solution (5 mmol/L CDCO in DMSO) was added into 5 mL E3 medium, then 16 hpf zebra fish embryos were gently transferred to this medium (solution) and incubated at 28.5° C. for 30 min. The dyes which stick to the chorion of the embryos were washed away with E3 medium before imaging by fluorescence microscopy.

For the example represented by FIGS. 3-8, the zebra fish embryos at 2.5 hpf, 4.5 hpf, 6.5 hpf, 7.5 hpf, 8.5 hpf, 11.5 hpf and 16.5 hpf were separately handled following the same procedure.

For the example represented by FIG. 22, the staining time required was 1 hour, since the CDCO was more difficult to penetrate through the older fish skin. Before imaging, the zebrafish were treated with tricaine (anesthetic 0.03%).

For the example represented by FIGS. 9-12, the 4.5 hpf and 17.5 hpf zebrafish embryos were firstly incubated in an E3 medium containing 10 μM CDCO and 0.2% DMSO for 0.5 h, then were washed with E3 medium, followed by incubating in the E3 medium for 1 hour.

All the zebrafish were imaged using fluorescent microscopy (Axio. Vert with X-Cite Series 120Q). The blue-CH filter: excitation 365 nm, beam splitter FT 395 nm, emission 445/50 nm. The green-CH filter: excitation 450-490 nm, beam splitter FT 510 nm, emission 515-565 nm. The red-CH filter: excitation 587/25 nm, beam splitter FT 605 nm, and emission 647/70 nm.)

All animal related procedures were approved by the Care and Use of Animals in Research Committee at the University of Akron.

Protein Detection

This example examines the flavone dyes 1-6 in FIGS. 14 and 23. As described herein, the sensors exhibited a dramatic fluorescence turn-on upon selectively binding to serum albumin. Since the non-bound flavone dye is non-fluorescent in a hydrophilic environment, the dramatic fluorescence turn-on enabled direct coloration of serum albumin on the polyacrylamide gel without the need for "washing off" the free dye. This finding thus allows for selective protein staining for SDS-PAGE.

Flavone dyes 1-6 in FIGS. 14 and 23 were prepared, in order to examine the impact of the fine structures on their response properties. The first structure can be used with substituents 1-3 to form dyes 1-3, the second structure is dye 4, and the third structure can be used with substituents 5 and 6 to form dyes 5 and 6. The synthesis details are given below.

2-(4-(dimethylamino)phenyl)-3-hydroxy-4H-chromen-4-one (Dye 1)

4-(dimethylamino)benzaldehyde (10 mmol) was added to a solution of 1-(2-hydroxyphenyl)ethanone (10 mmol) in ethanol (20 mL) and aqueous NaOH (3 g in 10 mL water). The mixture was stirred at 50° C. for 12 h. The reaction mixture was cooled to room temperature, and neutralized with 1M HCl. The solid precipitate was collected by filtration, and then washed with water and a small amount of ethanol. The solid was dissolved in 20 mL ethanol and aqueous NaOH (3 g in 10 ml water). The reaction mixture was placed in an ice-water bath and 5 mL of 30% $H_2O_2$ solution was slowly added. The resulting mixture was stirred at room temperature overnight. Then, the mixture was neutralized with 1M HCl resulting in the gradual formation of precipitation. The crude product was recrystallized from ethanol. Yield=41%. $^1$H NMR (d6-DMSO, 300 MHz): δ=8.13 (d, 2H, J=9.3), 8.09 (d, 1H, J=8.4), 7.77 (m, 2H), 7.45 (m, 1H), 6.85 (d, 2H, J=9.3), 3.00 (s, 6H). $^{13}$C NMR (d6-DMSO, 75 MHz): 172.4, 154.7, 151.5, 147.3, 137.7, 133.5, 129.4, 125.1, 124.7, 121.9, 118.6, 118.4, 111.8, 40.1.

2-(4-(dimethylamino)phenyl)-6-(ethoxymethyl)-3-hydroxy-4H-chromen-4-one (Dye 2)

2'-hydroxyacetophenone (100 mmol) was added into 25 ml of concentrated hydrochloric acid containing 150 mmol of paraformaldehyde. The reaction mixture was maintained at room temperature with stirring for 48 h until a precipitate formed. Then the solid product was collected by suction filtration, washed with an aqueous solution of sodium bicarbonate, and then washed with water to get a product of 1-(5-(chloromethyl)-2-hydroxyphenyl)ethanone.

1-(5-(chloromethyl)-2-hydroxyphenyl)ethanone (10 mmol) was added into 20 ml of ethanol, then 10 mL water solution containing 3 g NaOH was added into the mixture. The mixture was reflux for 2 hours. The product solution containing 1-(5-(ethoxymethyl)-2-hydroxyphenyl)ethanone was cooled to room temperature and used for the next step without further purification.

To the 1-(5-(ethoxymethyl)-2-hydroxyphenyl)ethanone solution, 10 mmol of 4-(dimethylamino)benzaldehyde in 10 mL EtOH was added. The mixture was stirred at 50° C. for 4 h, and then cooled to room temperature. 2 g of NaOH in 5 ml water was added into the mixture. Then reaction mixture was placed in an ice-water bath and 5 mL of 30% $H_2O_2$ solution was slowly added. The resulting mixture was stirred at room temperature for overnight. Then, the mixture was neutralized with 1M HCl resulting in the gradual formation of precipitation. The crude product was recrystallized twice from ethanol/hexane. Yield=8%. $^1$H NMR (d6-DMSO, 300 MHz): δ=8.13 (d, 2H, J=9.0), 8.00 (s, 1H), 7.68 (s, 2H), 6.85 (d, 2H, J=9.0), 4.57 (s, 2H), 3.56 (m, 2H), 3.01 (s, 6H), 1.20 (t, 3H). $^{13}$C NMR (d6-DMSO, 75 MHz): 172.4, 154.0, 151.5, 147.3, 137.7, 135.4, 132.8, 129.4, 121.5, 118.6, 111.8, 111.5, 71.2, 65.6, 40.1, 15.6.

2-(4-(dimethylamino)phenyl)-3-hydroxy-6-methyl-4H-chromen-4-one (Dye 3)

4-methylphenol (100 mmol) in 20 mL of toluene was heated to melting, and 100 mmol of acetyl chloride was slowly added under vigorously stirring. Then the mixture was cooled to room temperature with an ice-water bath. The anhydrous $AlCl_3$ (200 mmol) was added in three portions. After the addition of $AlCl_3$, the reaction mixture was heated to 120° C. for 10 hours, and then was hydrolyzed by crushed ice. The oil layer was extracted with $CH_2Cl_2$ and dried with anhydrous $Na_2SO_4$, and the solvent was removed under reduced pressure. The crude product of 1-(2-hydroxy-5-methylphenyl)ethanone was purified by column chromatography on silica gel.

10 mmol of 1-(2-hydroxy-5-methylphenyl)ethanone was added to a solution of 4-(dimethylamino)benzaldehyde (10 mmol) in ethanol (20 mL) and aqueous NaOH (3 g in 10 mL water). The mixture was stirred at 50° C. for 4 h. The reaction mixture was cooled to room temperature, and neutralized with 1M HCl. The solid precipitate was collected by filtration, washed with water and a small amount of ethanol. The solid was dissolved in 20 mL ethanol and aqueous NaOH (3 g in 10 ml water). Then reaction mixture was placed in an ice-water bath and 5 mL of 30% $H_2O_2$ solution was slowly added. The resulting mixture was stirred at room temperature overnight. Then, the mixture was neutralized with 1M HCl resulting in the gradual formation of precipitation. The crude product was recrystallized from ethanol. Yield=34%. $^1$H NMR (d6-DMSO, 300 MHz): δ=8.11 (d, 2H, J=9.3), 7.86 (s, 1H), 7.63 (m, 2H), 6.85 (d, 2H, J=9.3), 3.01 (s, 6H), 2.43 (s, 3H). $^{13}$C NMR (d6-DMSO, 75 MHz): 172.3, 153.1, 151.4, 147.1, 137.6, 134.7, 134.1, 129.3, 124.2, 121.6, 118.5, 111.8, 40.1, 20.9.

2-(4-(dimethylamino)phenyl)-3-methoxy-6-methyl-4H-chromen-4-one (Dye 4)

2 mmol of 2-(4-(dimethylamino)phenyl)-3-hydroxy-6-methyl-4H-chromen-4-one was dissolved in 10 mL of acetone, followed by 3 mmol of $K_2CO_3$. The reaction mixture was placed in the ice-water bath, and then 3 mmol of Me2SO4 was added dropwise. The mixture was stirred for 24 hours until the mixture color was changed from dark yellow to light yellow. 20 mL of water was added to terminate the reaction. The mixture was extracted with 3×20 ml of $CH_2Cl_2$, dried with $Na_2SO_4$, and evaporated by reduced pressure. The product was obtained by column chromatography on silica gel(Hexane/$CH_2Cl_2$=9/1). Yield=81%. $^1$H NMR (d6-DMSO, 300 MHz): δ=8.01 (dd, 2H, $J_1$=9.0, $J_2$=1.8), 7.83 (s, 1H), 7.58 (m, 2H), 6.85 (dd, 2H, $J_1$=9.0, $J_2$=1.8), 3.77 (s, 3H) 3.02 (s, 6H), 2.42 (s, 3H). $^{13}$C NMR (d6-DMSO, 75 MHz): 173.5, 153.2, 152.1, 139.6, 135.1, 134.6, 129.9, 124.4, 123.7, 120.8, 118.4, 117.2, 111.9, 59.6, 40.0, 20.9.

N-(4-(3-hydroxy-4-oxo-4H-chromen-2-yl)phenyl) acetamide (Dye 5)

10 mmol of N-(4-formylphenyl)acetamide was added to a solution of 1-(2-hydroxyphenyl)ethanone (10 mmol) in ethanol (20 mL) and aqueous NaOH (3 g in 10 ml water). The mixture was stirred at room temperature for overnight. The reaction mixture was neutralized with 1M HCl, and the solid precipitate was collected by filtration. The solid was dissolved in 20 mL ethanol and aqueous NaOH (3 g in 10 mL water). Then reaction mixture was placed in an ice-water bath and 5 mL of 30% $H_2O_2$ solution was slowly added. The resulting mixture was stirred at room temperature overnight. The precipitate was observed and collected by filtration, washed with water. The crude product was recrystallized from ethanol/$CH_2Cl_2$. Yield=59%. $^1$H NMR (d6-DMSO, 300 MHz): δ=10.2 (s, 1H, OH), 8.22 (d, 2H, J=8.7), 8.10 (d, 1H, J=7.8), 7.77 (m, 4H), 7.46 (m, 1H), 2.08 (s, 3H). $^{13}$C NMR (d6-DMSO, 75 MHz): 173.2, 169.2, 154.9, 145.7, 141.2, 139.0, 134.0, 128.8, 126.1, 125.2, 124.9, 121.8, 118.9, 118.8, 24.6.

2-(4-aminophenyl)-3-hydroxy-4H-chromen-4-one (Dye 6)

5 mmol of N-(4-(3-hydroxy-4-oxo-4H-chromen-2-yl) phenyl)acetamide was dissolved in 5 mL THF, then 25 ml of 37% HCl solution was added into the reaction mixture. The mixture was refluxed for 48 hours, and then was neutralized by $Na_2CO_3$. 3×20 ml of $CH_2Cl_2$ was used to extract the mixture, washed with brine and water, and then dried under $Na_2SO_4$. The desired product was purified by column chromatography on silica gel (Hexane/$CH_2Cl_2$=4/1). Yield=84%. $^1$H NMR (d6-DMSO, 300 MHz): δ=8.12 (m, 3H), 7.81 (m, 2H), 7.48 (m, 1H), 6.99 (d, 2H, J=8.4), 5.11 (broad peak, hydrogen bond). $^{13}$C NMR (d6-DMSO, 75 MHz):173.1, 154.9, 145.6, 139.8, 138.9, 134.0, 129.5, 126.8, 125.2, 125.0, 121.8, 120.3, 118.7.

Results

The absorbance and fluorescence spectra of compounds 1-6 in dimethyl sulfoxide (DMSO) were investigated and the results are in Table 1.

TABLE 1

Comparison of spectroscopic properties of compounds 1-6 in DMSO. (λabs and λem: unit = nm)

|   | λabs | λem | Φ/% |
|---|---|---|---|
| 1 | 403 | 518, 578 | 10.0 |
| 2 | 403 | 521, 584 | 14.1 |
| 3 | 404 | 518, 584 | 11.0 |
| 4 | 390 | 504 | 37.6 |
| 5 | 363 | 505 | 5.4 |
| 6 | 394 | 501, 575 | 7.2 |

The fluorescence of the compound 1 revealed positive solvatochromism (i.e. emission red-shifted with increasing solvent polarity). As shown in FIGS. 15 and 16, the flavone 1 gave two fluorescence bands corresponding to the excited normal form (N*) and the tautomeric form (T*) associated with excited state intramolecular proton transfer (ESIPT). Upon excitation via photon irradiation, the dipole moment increased dramatically because of the charge transfer from D-A structure in compound 1. An increase in the solvent polarity could relax the excited molecules more efficiently, thus decreasing the energy of the excited state of fluorophore and resulting in a red-shifted emission. FIGS. 15 and 16 show that both N* and T* emission wavelengths of compound 1 correlated well with the relative solvent polarity. The fluorescence of compound 1 was nearly 100% quenched by water due to intermolecular electron or proton transfer. Non-fluorescence in water raises the possibility of eliminating the washing process in the protein detection procedure, since the free dye molecules gives negligible background signal in water.

The fluorescence of flavone 1 was found to exhibit remarkable fluorescence enhancement upon addition of bovine serum albumin (BSA) (FIGS. 15 and 16), showing a great potential for sensor applications. In the aqueous buffer (0.5% DMSO, 10 mM of PBS, pH=7.4), the BSA binding-induced fluorescence turn-on was so large that it could be easily seen by naked eye. Improved response was observed from flavone derivatives 2, 3, and 4, as they gave almost no fluorescence in the absence of BSA (FIGS. 15-17). Higher fluorescence response from compounds 2-4 indicated that the alkyl substituent at the 6-position of flavone derivatives could have a large impact on the flavone-water and flavone-protein interactions. Higher fluorescence response from compounds 2-4, in comparison with compound 6, also indicated that the amino group should be covered with the alkyl groups. The intramolecular charge transfer along the D-A conjugated backbone plays a very important role in the environment-sensitivity of the flavone. All the evidence consistently pointed to the flavone dye entering the hydrophobic site of BSA. In addition, the fluorescence intensities of flavone dyes revealed good linear correlation with BSA concentration ranging from 0 to 1.0 mg/mL.

Generally, the detection limit can be defined as the analyte concentration at which a 10% increase in fluorescence emission can be measured. In this example, the fluorescence enhancement of compounds 1-6 in the presence of 1.0 mg/mL of BSA was 7 ~1100 fold, as seen in Table 2.

TABLE 2

Comparison of spectroscopic properties of compounds 1-6 with or without BSA. [1-6] = 10 μM, [BSA] = 1.0 mg/ml, 10 mM PBS buffer solution containing 0.5% DMSO, pH = 7.4.

|   | 1 | 2 | 3 | 4 | 5 | 6 |
|---|---|---|---|---|---|---|
| $\lambda abs_{(-)}{}^a$ | 403 | 410 | 400 | 398 | 357 | 373 |
| $\lambda abs_{(+)}{}^a$ | 416 | 415 | 409 | 398 | 365 | 386 |
| $\lambda em_{(-)}{}^a$ | 560 | 555 | 582 | 490 | 452 | 522 |
| $\lambda em_{(+)}{}^a$ | 556 | 506 | 552 | 484 | 514 | 512 |
| $F_{(+)}/F_{(-)}{}^b$ | 38 | 740 | 170 | 1100 | 7.0 | 29 |

$^a$unit = nm, $_{(+)}$= with BSA, $_{(-)}$= without BSA;
$^b F_{(+)}$ = fluorescence intensity at $\lambda em_{(+)}$, $F_{(-)}$ = fluorescence intensity at $\lambda em_{(-)}$.

Therefore, the detection limits of compounds 1-6 were 2.6, 0.14, 0.59, 0.09, 14, and 3.4 μg/mL, respectively. For Off/On type fluorescent sensor, the Signal-to-Noise (S/N) ratio above 3:1 is considered reliable for visual evaluation. The visual recognizable detection limits of compounds 1-6 were calculated as 78, 4.2, 17.7, 2.7, 420, and 102 μg/mL, respectively. The reference range for serum albumin concentration in human blood plasma is approximately 35-50 mg/mL. Even in fish, the concentration of serum albumins can reach 0.5-5 mg/mL. The detection limits of the compounds were much lower than serum albumin concentration, indicating the capability for actual blood sample testing.

The photostability of flavone dyes 1-6 in the presence of BSA was also examined to evaluate the application for long-term imaging. The dye-BSA complexes (10 μM of compounds 1-6, 1.0 mg/mL of BSA in 10 mM PBS buffer containing 0.5% DMSO, pH=7.4) were placed in cuvette cells, then were continuously irradiated under a hand-held UV lamp (λ=365 nm, 500 μW/cm2). Although the fluorescence quenching of compound 5 and 6 was observed, the fluorescence intensities of compounds 1-4 could retain above 80% of their original intensities after one hour continuous UV excitation.

In real blood sample or proteins extraction from tissues, there are many different proteins which will cause serious interference with the detection result. Thus, the high selectivity towards the target protein over the other competitive proteins can be of importance for fluorescence probes. The fluorescence response of compounds 1-6 to various proteins in PBS buffer was investigated and the results are shown in FIG. 17. Under the same conditions, the fluorescence enhancement in the presence of BSA was much larger than that in the presence of other proteins: collagen, gelatin, fibrinogen, lysozyme, trypsin and lipase. For all these flavone dyes, the fluorescence response to other proteins was lower than 20% of that to BSA. The high selectivity could be attributed to the specific binding of flavone dyes to the hydrophobic pockets in the BSA structure.

Serum albumin is known as the most abundant protein in blood serum. The probe's fluorescence response to serum albumin in real blood samples would be considered as an ideal sensing tool. In this example, 10 μM of compound 4 was dissolved in 1 mL of PBS buffer as a test solution. Upon addition of initial monkey serum to the test solution, the fluorescence of compound 4 was rapidly increased, as shown in FIGS. 18 and 19, then gradually reached equilibrium with the 5 μL of serum, and eventually became very intense blue-green emission. The fluorescence intensity of compound 4 at 505 nm was enhanced up to 135-fold in the presence of 25 μL of serum sample and showed linear response to monkey serum concentration ranging from 0 to 1 μL/mL. The detection limit (S/N>3) for monkey serum was calculated as 0.03 μL. The result demonstrated that the probe was capable of estimating the albumin concentration in monkey serum samples.

To demonstrate the feasibility of a wash-free method for protein imaging in polyacrylamide gels, compound 4 was directly used to stain the electrophoresis gel. Various proteins were run on the 1-D SDS-PAGE minigels with running buffer (25 mM Tris, 192 mM glycine, 0.1% SDS pH 8.3) under 100 volts for 1.5 hrs. The minigels were then placed in the dye solution (10 mM of compound 4, 0.3% SDS, and AcOH/DMSO/H2O=5:10:85). FIG. 20 shows the fluorescent images of the gel containing BSA (0.1 μg, 1 μg, 10 μg, and 100 μg), 10 μg of human serum albumin (HSA), fibrinogen, lysozyme, and trypsin after 2 hours staining by compound 4. It was found that BSA was efficiently stained and clearly observed at very low concentration (~1 μg) under a UV lamp. The serum albumin proteins were selectively stained because HSA had similar folding structure as BSA. The fluorescence pattern of proteins in the gel exhibited acceptable contrast ratio without a washing process. Although the fluorescence background could be reduced by washing, the free dyes showed much weaker fluorescence in an aqueous medium and in gels, in comparison with commercial SYPRO Ruby. Therefore, the discovered protein-staining reagent had the following advantages: (1) low interference of SDS to fluorescence, thereby eliminating the pretreatment; (2) very weak fluorescent in water and gels to eliminate the need for the washing process; (3) strong interaction with the proteins (serum albumin) to reduce the staining time; (4) a high signal-to-noise (S/N) ratio for the high contrast ratio of images.

Various modifications and alterations that do not depart from the scope and spirit of this invention will become apparent to those skilled in the art. This invention is not to be duly limited to the illustrative embodiments set forth herein.

What is claimed is:

1. A flavonoid compound for imaging zebrafish embryos, zebrafish larva, and/or zebrafish blood vessels, where the flavonoid compound is defined by the formula

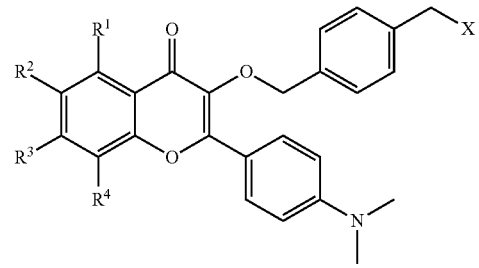

where each $R^1$-$R^4$ is individually an organic group or a hydrogen atom and X is a halogen atom.

2. The flavonoid of claim 1, where the flavonoid compound is defined by the formula

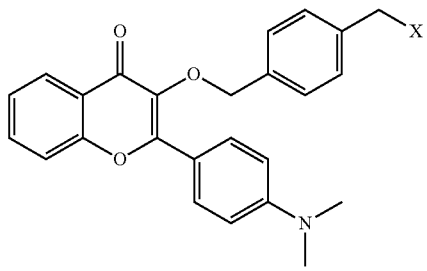

where X is a halogen atom.

3. The flavonoid of claim 1, where the flavonoid compound is defined by the formula

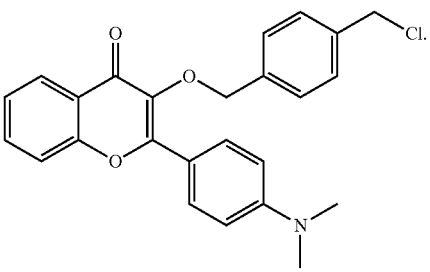

4. The flavonoid of claim 1, where each of $R^1$-$R^4$ is individually an alkyl group or a hydrogen atom.

5. A method of imaging a zebrafish comprising:

providing an embryo media;

adding a flavonoid compound to the embryo media, where the flavonoid compound is defined by the formula

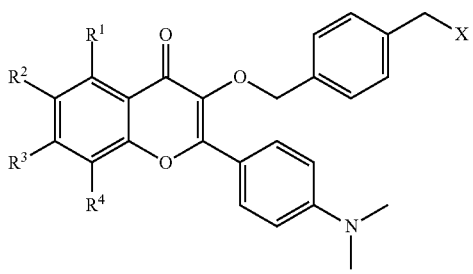

where each $R^1$-$R^4$ is individually an organic group or a hydrogen atom and X is a halogen atom;
adding a zebrafish embryo to the embryo media;
allowing the flavonoid compound to permeate into the zebrafish embryo;
optionally allowing the zebrafish embryo to develop into a zebrafish larva;
exciting the zebrafish embryo and/or zebrafish larva with an excitation wavelength that excites the flavonoid compound and induces a fluorescence response; and
capturing an image of the zebrafish embryo, the zebrafish larva, or both the zebrafish embryo and the zebrafish larva.

6. The method of claim 5, where the zebrafish embryo is at from about 4 to about 170 hours post fertilization when it is added to the embryo media.

7. The method of claim 5, where the embryo media is E3 media.

8. The method of claim 5, where the zebrafish embryo includes a yolk syncytial layer and the flavonoid compound selectively stains the yolk syncytial layer.

9. The method of claim 5, where the excitation wavelength is from about 550 nm to about 570 nm or from about 400 nm to about 460 nm.

10. The method of claim 5, where the zebrafish embryo develops into a zebrafish larva.

11. The method of claim 5, where each of $R^1$-$R^4$ is individually an alkyl group or a hydrogen atom.

12. The method of claim 5, where the flavonoid compound is defined by the formula

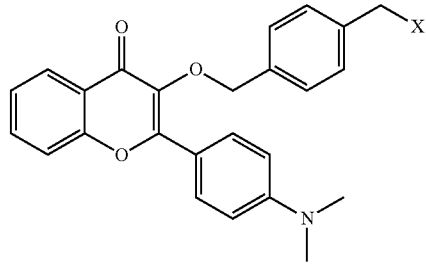

where X is a halogen atom.

13. The method of claim 5, where the flavonoid compound is defined by the formula

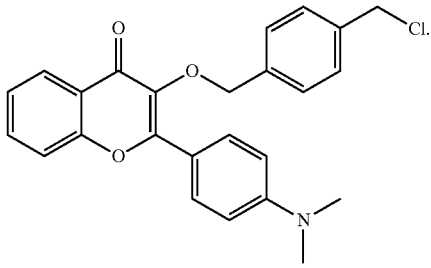 [SMILES: CN(C)c1ccc(-c2oc3ccccc3c(=O)c2OCc2ccc(CCl)cc2)cc1]

14. A method of imaging zebrafish blood vessels comprising:
providing an embryo media;
adding a flavonoid compound to the embryo media, where the flavonoid compound is defined by the formula

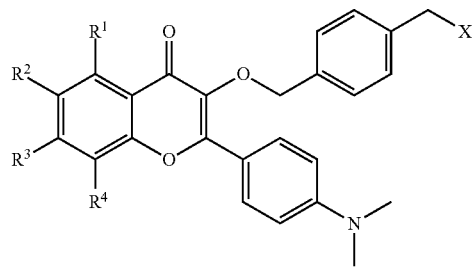

where each $R^1$-$R^4$ is individually an organic group or a hydrogen atom and X is a halogen atom;
adding a zebrafish of about 72 to about 108 hours post fertilization to the embryo media;
allowing the flavonoid compound to permeate into the zebrafish;
exciting the zebrafish with an excitation wavelength that excites the flavonoid compound and induces a fluorescence response; and
capturing an image of the zebrafish.

15. The method of claim 14, where the step of allowing the flavonoid compound to permeate into the zebrafish takes from about 6 to about 8 hours.

* * * * *